(12) United States Patent
Milton et al.

(10) Patent No.: US 8,084,590 B2
(45) Date of Patent: *Dec. 27, 2011

(54) LABELLED NUCLEOTIDES

(75) Inventors: John Milton, Nr. Saffron Walden (GB);
Silke Ruediger, Nr. Saffron Walden (GB); Xiaohai Liu, Nr. Saffron Walden (GB)

(73) Assignee: Illumina Cambridge Limited, Nr. Saffron Walden, Essex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/803,163

(22) Filed: Jun. 21, 2010

(65) Prior Publication Data

US 2010/0311178 A1    Dec. 9, 2010

Related U.S. Application Data

(63) Continuation of application No. 12/220,682, filed on Jul. 24, 2008, now Pat. No. 7,795,424, which is a continuation of application No. 10/525,399, filed as application No. PCT/GB03/003690 on Aug. 22, 2003, now Pat. No. 7,414,116, which is a continuation-in-part of application No. 10/227,131, filed on Aug. 23, 2002, now Pat. No. 7,057,026.

(51) Int. Cl.
*C07G 11/00* (2006.01)
*C07H 21/04* (2006.01)
*C07H 19/04* (2006.01)
*C12Q 1/68* (2006.01)

(52) U.S. Cl. ............ 536/4.1; 536/23.1; 536/26.6; 435/6

(58) Field of Classification Search ................... 536/4.1, 536/23.1, 26.6; 435/6
See application file for complete search history.

(56) References Cited

U.S. PATENT DOCUMENTS

| | | | |
|---|---|---|---|
| 4,711,955 | A | 12/1987 | Ward et al. |
| 4,772,691 | A | 9/1988 | Herman |
| 5,302,509 | A | 4/1994 | Cheeseman |
| 5,436,143 | A | 7/1995 | Hyman |
| 5,516,664 | A | 5/1996 | Hyman |

(Continued)

FOREIGN PATENT DOCUMENTS

WO    WO 91/06678    5/1991

(Continued)

OTHER PUBLICATIONS

Oksman, P. et al, Solution conformations and hydrolytic stability of 2'- and 3'-substituted 2', 3'-dideoxyribonucleosides, including some potential inhibitors of human immunodeficiency virus, Journal of Physical Organic Chemistry, 1992, vol. 5, No. 11, pp. 741-747.

(Continued)

*Primary Examiner* — Jezia Riley
(74) *Attorney, Agent, or Firm* — Jones Day

(57) ABSTRACT

The invention provides a nucleotide or nucleoside having a base attached to a detectable label via a cleavable linker, characterised in that the cleavable linker contains a moiety selected from the group comprising: Formula (I) (wherein X is selected from the group comprising O, S, NH and NQ wherein Q is a $C_{1-10}$ substituted or unsubstituted alkyl group, Y is selected from the group comprising O, S, NH and N(allyl). T is hydrogen or a $C_{1-10}$ substituted or unsubstituted alkyl group and * indicates where the moiety is connected to the remainder of the nucleotide or nucleoside).

19 Claims, 4 Drawing Sheets

Uridine C5-linker

Cytidine C5-linker

N7 Deazaadenosine C7-linker

N7 Deazaguanosine C7-linker

Adenosine N6-linker

Cytidine N4-linker where $R_1$ and $R_2$, which may be the same or different, are each selected from H, OH, or any group which can be transformed into an OH. Suitable groups for $R_1$ and $R_2$ are described in Figure 3

X = H, phosphate, diphosphate or triphosphate

Guanosine N2-linker

U.S. PATENT DOCUMENTS

| | | | |
|---|---|---|---|
| 5,547,839 | A | 8/1996 | Dower et al. |
| 5,602,000 | A | 2/1997 | Hyman |
| 5,763,594 | A | 6/1998 | Hiatt et al. |
| 5,872,244 | A | 2/1999 | Hiatt et al. |
| 6,008,379 | A | 12/1999 | Benson et al. |
| 6,087,095 | A | 7/2000 | Rosenthal et al. |
| 6,214,987 | B1 | 4/2001 | Hiatt et al. |
| 6,255,475 | B1 | 7/2001 | Kwiatkowski |
| 7,414,116 | B2 * | 8/2008 | Milton et al. ............... 536/23.1 |

FOREIGN PATENT DOCUMENTS

| | | |
|---|---|---|
| WO | WO 92/10587 | 6/1992 |
| WO | WO 94/14972 | 7/1994 |
| WO | WO 96/07669 | 3/1996 |
| WO | WO 99/05315 | 2/1999 |
| WO | WO 99/57321 | 11/1999 |
| WO | WO 00/02895 | 1/2000 |
| WO | WO 0015844 | 3/2000 |
| WO | WO 00/53812 | 9/2000 |
| WO | WO 01/23610 | 4/2001 |
| WO | WO 01/57249 | 8/2001 |
| WO | WO 02/29003 | 4/2002 |

OTHER PUBLICATIONS

Zavgorodny, S. et al, 1-Alkylthioalkylation of nucleoside hydroxyl functions and its synthetic applications: a new versatile method in nucleoside chemistry, Tetrahedron Letters, 1991, vol. 32, No. 51, pp. 7593-7596.

Oksman, P. et al, Conformation of 3'-substituted 2', 3'-dideoxyribonucleosides in aqueous solution: nucleoside analogues with potential antiviral activity, Nucleosides & Nucleotides, 1991, vol. 10, No. 1-3, pp. 567-568.

M. Kloosterman, J.H. Van Boom, P. Chatelard, P. Boullanger, and G. Descotes, The Relative Stability of Allyl Ether, Allyloxycarbonyl Ester and Prop-2 Enylidene Acetal protective groups toward Iridium, Rhodium and Palladium Catalysts., Tetrahedron Letters, vol. 26, No. 41, (pp. 5045-5048) 1985.

Kocienski, Protecting Groups, Georg Tieme Verlag, Stuttgart, (pp. 61-68) 1994.

G.H. Veeneman, G.A. Van Der Marel, H. Van Den Elst and J.H. Van Boom, An Efficient Approach to The Synthesis of Thymidine Derivatives Containing Phosphate-Isosteric Methylene Acetal Linkages, vol. 47, No. 8 (pp. 1547-1562) 1991.

Masato Kitamura, Shinji Tanaka and Masahiro Yoshimura, CpRu -Catalyzed Deprotrctopn of Allyl Carboxylic Esters, American Chemistry Society, vol. 67 No. 14, (pp. 4975-4977) 2002.

Francois Guibe, Allylic Protecting Groups and Their use in a Complex Environment Part II: Allylic Protecting Groups and Their Removal Through Catalytic Palladium Allyl Methodology, Tetrahedron NL vol. 53 No. 13, (pp. 2967-3042) 1997.

Yoshihiro Hayakawa, Masaaki Hiroea and Ryoji Noyori, Allyl Protection of Guanine and Thymine Residues in Oligodeoxyribonucleotides, J of Organometallic Chemistry, vol. 58 JOC, (pp. 5551-5555) 1993.

Francois Guibe, Allylic Protecting Groups and Their use in a Complex Environment Part I: Allylic Protection of Alcohols, Tetrahedron NL, vol. 53 No. 40, (pp. 13509-13556) 1997.

Frank Bergmann, Erich Kueng, Patrick Iaiza and Willi Bannwarth, Allyl as Internucleotide Protecting Group in DNA Synthesis to be Cleaved off by Ammonia, Tetrahedron NL, vol. 51 No. 25 (pp. 6971-6976) 1995.

Green, Protective Groups in Organic . . . , John Wiley & Sons NY, (pp. 67-74 & 574-576) 1999.

J. Brunckova et al., Tetrahedron Letters, (1994), vol. 35, pp. 6619-6622.

S. Nishino et al., Heteroatom Chemistry, (1991), vol. 2, pp. 187-196.

M. Krečmerováet al., Collect. Czech. Chem. Commun., (1990), vol. 55, pp. 2521-2536.

P. J. L. M. Quaedflieg et al., Tetrahedron Letters, (1992), vol. 33, No. 21, pp. 3081-3084.

J. I. Yamashita et al., Chem Pharm. Bull., (1987), vol. 35, pp. 2373-2381.

S.G. Zavgorodny et al., Nucleosides, Nucleotides & Nucleic Acids, (2000), 19(10-12), 1977-1991.

Kraevskii et al., Substrate Inhibitors of DNA Biosynthesis, Translated from Molekulyarnaya Biologiya [Mol. Bio. (Mosk.)] 21:33-38 (1987).

Henner et al., Enzyme Action at 3' Termini of Ionizing Radiation-induced DNA Strand Breaks, The Journal of Biological Chemistry, 258:15198-15205 (1983).

* cited by examiner

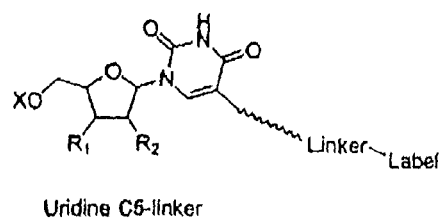
Uridine C5-linker

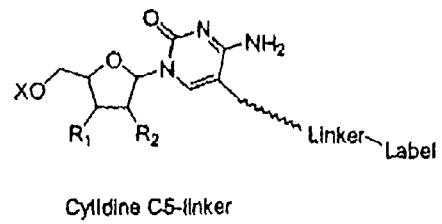
Cytidine C5-linker

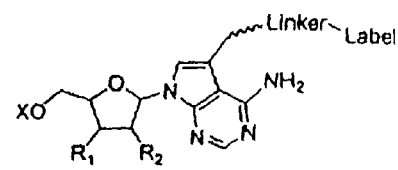
N7 Deazaadenosine C7-linker

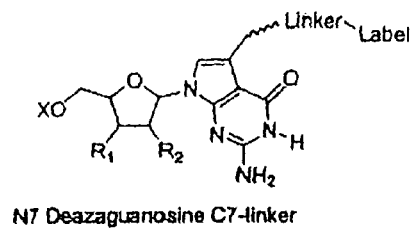
N7 Deazaguanosine C7-linker

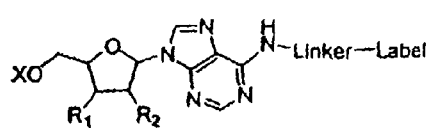
Adenosine N6-linker

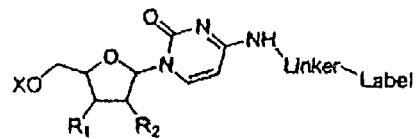
Cytidine N4-linker where $R_1$ and $R_2$, which may be the same or different, are each selected from H, OH, or any group which can be transformed into an OH. Suitable groups for $R_1$ and $R_2$ are described in Figure 3

X = H, phosphate, diphosphate or triphosphate

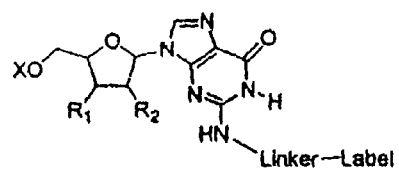
Guanosine N2-linker

Fig. 1

Label ∼∼Cleavable linker∼∼∼Base

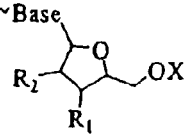

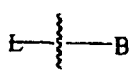

Cleavable linkers may include:

where $R_1$ and $R_2$, which may be the same or different, are each selected from H, OH, or any group which can be transformed into an OH, including a carbonyl

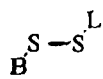

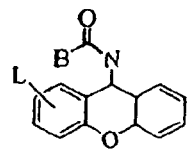

$R_1$ and $R_2$ groups may include

 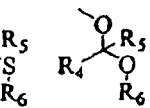 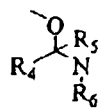 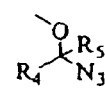

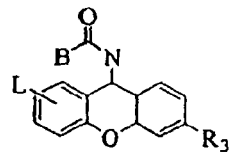

   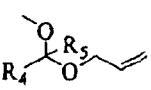

R3 represents one or more substituents independently selected from alkyl, alkoxy, amino or halogen

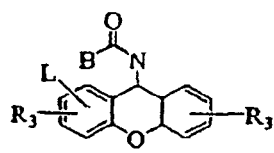

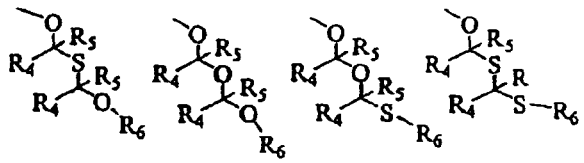

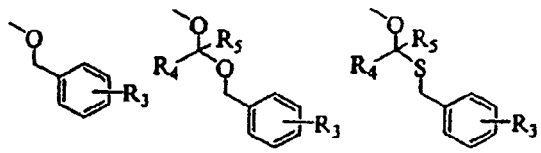

where $R_4$ is H or alkyl, $R_5$ is H or alkyl and $R_6$ is alkyl, cycloalkyl, alkenyl, cycloalkenyl or benzyl and X is H, phosphate, diphosphate or triphosphate

Fig. 3

LABELLED NUCLEOTIDES

CROSS REFERENCE TO RELATED APPLICATIONS

The present application is a Continuation Application of U.S. application Ser. No. 12/220,682, filed Jul. 24, 2008 now U.S. Pat. No. 7,795,424, which is a Continuation Application of U.S. application Ser. No. 10/525,399, filed Feb. 23, 2005, now U.S. Pat. No. 7,414,116, which is a National Stage Application claiming the priority of PCT Application No. PCT/GB2003/003690, filed Aug. 22, 2003, which is a Continuation in Part Application of U.S. application Ser. No. 10/227,131, filed Aug. 23, 2002, now U.S. Pat. No. 7,057,026. Applicants claim the benefits of 35 U.S.C. §120 as to the PCT application and the U.S. applications, the entire disclosures of which applications are incorporated herein by reference in their entireties.

FIELD OF THE INVENTION

This invention relates to labelled nucleotides. In particular, this invention discloses nucleotides having a removable detectable label and their use in polynucleotide sequencing methods.

BACKGROUND

Advances in the study of molecules have been led, in part, by improvement in technologies used to characterise the molecules or their biological reactions. In particular, the study of the nucleic acids DNA and RNA has benefited from developing technologies used for sequence analysis and the study of hybridisation events.

An example of the technologies that have improved the study of nucleic acids, is the development of fabricated arrays of immobilised nucleic acids. These arrays consist typically of a high-density matrix of polynucleotides immobilised onto a solid support material. See, e.g., Fodor et al., *Trends Biotech*. 12:19-26, 1994, which describes ways of assembling the nucleic acids using a chemically sensitized glass surface protected by a mask, but exposed at defined areas to allow attachment of suitably modified nucleotide phosphoramidites. Fabricated arrays can also be manufactured by the technique of "spotting" known polynucleotides onto a solid support at predetermined positions (e.g., Stimpson et al., *Proc. Natl. Acad. Sci.* USA 92:6379-6383, 1995).

A further development in array technology is the attachment of the polynucleotides to the solid support material to form single molecule arrays. Arrays of this type are disclosed in International Patent App. WO 00/06770. The advantage of these arrays is that reactions can be monitored at the single molecule level and information on large numbers of single molecules can be collated from a single reaction.

For DNA arrays to be useful, the sequences of the molecules must be determined. U.S. Pat. No. 5,302,509 discloses a method to sequence polynucleotides immobilised on a solid support. The method relies on the incorporation of 3'-blocked bases A, G, C and T, each of which has a distinct fluorescent label, into the immobilised polynucleotide, in the presence of DNA polymerase. The polymerase incorporates a base complementary to the target polynucleotide, but is prevented from further addition by the 3'-blocking group. The label of the incorporated base can then be determined and the blocking group removed by chemical cleavage to allow further polymerisation to occur.

Welch et al. (*Chem. Eur. J.* 5(3):951-960, 1999) describes the synthesis of nucleotide triphosphates modified with a 3'-O-blocking group that is photolabile and fluorescent. The modified nucleotides are intended for use in DNA sequencing experiments. However, these nucleotides proved to be difficult to incorporate onto an existing polynucleotide, due to an inability to fit into the polymerase enzyme active site.

Zhu et al. (*Cytometry* 28:206-211, 1997) also discloses the use of fluorescent labels attached to a nucleotide via the base group. The labelled nucleotides are intended for use in fluorescence in situ hybridisation (FISH) experiments, where a series of incorporated labelled nucleotides is required to produce a fluorescent "bar code".

WO99/57321 describes the use of nucleotides comprising fluorophores linked to the nucleotide by chemically or photochemically cleavable linker moieties.

WO00/53812 and EP-A2-1 291 354 disclose nucleotide compounds of general structure Fluorophore-S—S-Linker-Nucleotide and their use in nucleic acid assay methods. WO00/53812 also makes reference to periodate cleavage of a cis-glycol linkage between nucleotide and fluorophore.

WO 01/92284 discloses the use of enzyme-cleavable groups linking blocking and reporting moieties to nucleotides. It is preferred that these enzyme-cleavable groups are the same, i.e. that both the blocking and reporter moieties are attached to the nucleotide by a chain comprising a group cleavable by a common enzyme. Cleavable groups described in WO 01/92284 are esters and amides, cleavable by esterases and amidases respectively.

WO02/29003 describes nucleotides analogues that contain a label linked through cleavable linkers to the nucleotide base, or an analogue of the base. Photocleavable linkers comprising 2-nitrobenzyl moieties are described.

SUMMARY OF THE INVENTION

The present inventors have surprisingly found that certain linkers which connect the bases of nucleotides to detachable labels, e.g. fluorophores, may be cleaved using water-soluble phosphines or water-soluble transition metal catalysts formed from a transition metal and at least partially water-soluble ligands. In aqueous solution the latter form at least partially water-soluble transition metal complexes.

Labelled nucleotides comprising such linkers an methods for using them are clearly advantageous in the context of techniques carried out in aqueous media such as sequencing reactions, polynucleotide synthesis, nucleic acid amplification, nucleic acid hybridization assays, single nucleotide polymorphism studies, and other techniques using enzymes such as polymerases, reverse transcriptases, terminal transferases, or other DNA modifying enzymes. The invention is especially useful in techniques that use labelled dNTPs, such as nick translation, random primer labeling, end-labeling (e.g., with terminal deoxynucleotidyltransferase), reverse transcription, or nucleic acid amplification.

According to a first aspect of the invention, there is provided a nucleotide or nucleoside having a base attached to a detectable label via a cleavable linker, characterised in that the cleavable linker contains a moiety selected from the group comprising:

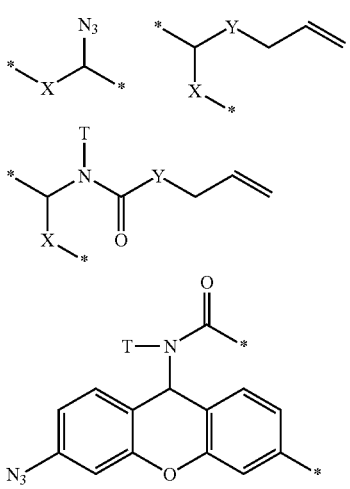

(wherein X is selected from the group comprising O, S, NH and NQ wherein Q is a $C_{1-10}$ substituted or unsubstituted alkyl group, Y is selected from the group comprising O, S, NH and N(allyl), T is hydrogen or a $C_{1-10}$ substituted or unsubstituted alkyl group and * indicates where the moiety is connected to the remainder of the nucleotide or nucleoside).

According to a second aspect of the invention, there is provided a method of cleaving a linker that contains a moiety selected from the groups comprising:

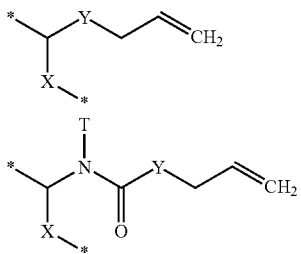

(wherein X is selected from the group comprising O, S, NH and NQ wherein Q is a $C_{1-10}$ substituted or unsubstituted-alkyl group, Y is selected from the group comprising O, S, NH and N(allyl), T is hydrogen or a $C_{1-10}$ substituted or unsubstituted alkyl group and * indicates where the moiety is connected to the remainder of a nucleotide or nucleoside), said linker being present in the nucleotide or nucleoside and connecting the base thereof to a detectable label, said method comprising contacting the nucleotide or nucleoside with a water-soluble phosphine-based transition metal catalyst.

According to a third aspect of the invention, there is provided a method of cleaving a linker that contains a moiety selected from the groups comprising:

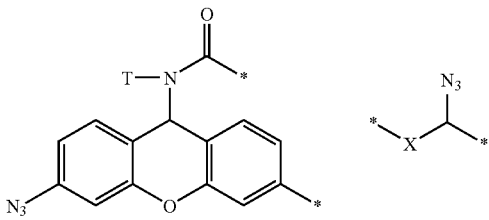

(wherein X is selected from the group comprising O, S, NH and NQ wherein Q is a $C_{1-10}$ substituted or unsubstituted alkyl group, T is hydrogen or a $C_{1-10}$ substituted or unsubstituted alkyl group and * indicates where the moiety is connected to the remainder of a nucleotide or nucleoside), said linker being present in the nucleotide or nucleoside and connecting the base thereof to a detectable label, said method comprising contacting the nucleotide or nucleoside with a water-soluble phosphine.

The method according to the second and third aspects of the invention are particularly useful in sequencing reactions. Such reactions constitute a further aspect of the invention. Viewed from this aspect, the invention provides a method for determining an identity of a nucleotide in a target single-stranded polynucleotide, comprising:

(a) providing one or more of the nucleotides A, G, C and T or U in which each of said nucleotides has a base that is attached to a distinct detectable label via a linker, said linker being cleavable with a water-soluble phosphine; and a nascent polynucleotide complementary to the target polynucleotide, one of said provided nucleotides being suitable for incorporation into said nascent polynucleotide;

(b) incorporating the nucleotide suitable for incorporation into said nascent polynucleotide; and (c) carrying out a method according to the second or third aspect of the invention.

DESCRIPTION OF THE DRAWINGS

FIG. 1 shows exemplary nucleotide structures useful in the invention. For each structure, X can be H, phosphate, diphosphate or triphosphate. $R_1$ and $R_2$ can be the same or different, and can be selected from H, OH, or any group which can be transformed into an OH.

FIG. 3 is a schematic illustration of some of the 2' or 3' OH blocking groups which can be present in the nucleotides or nucleosides according to the invention.

DETAILED DESCRIPTION

Figure 2:
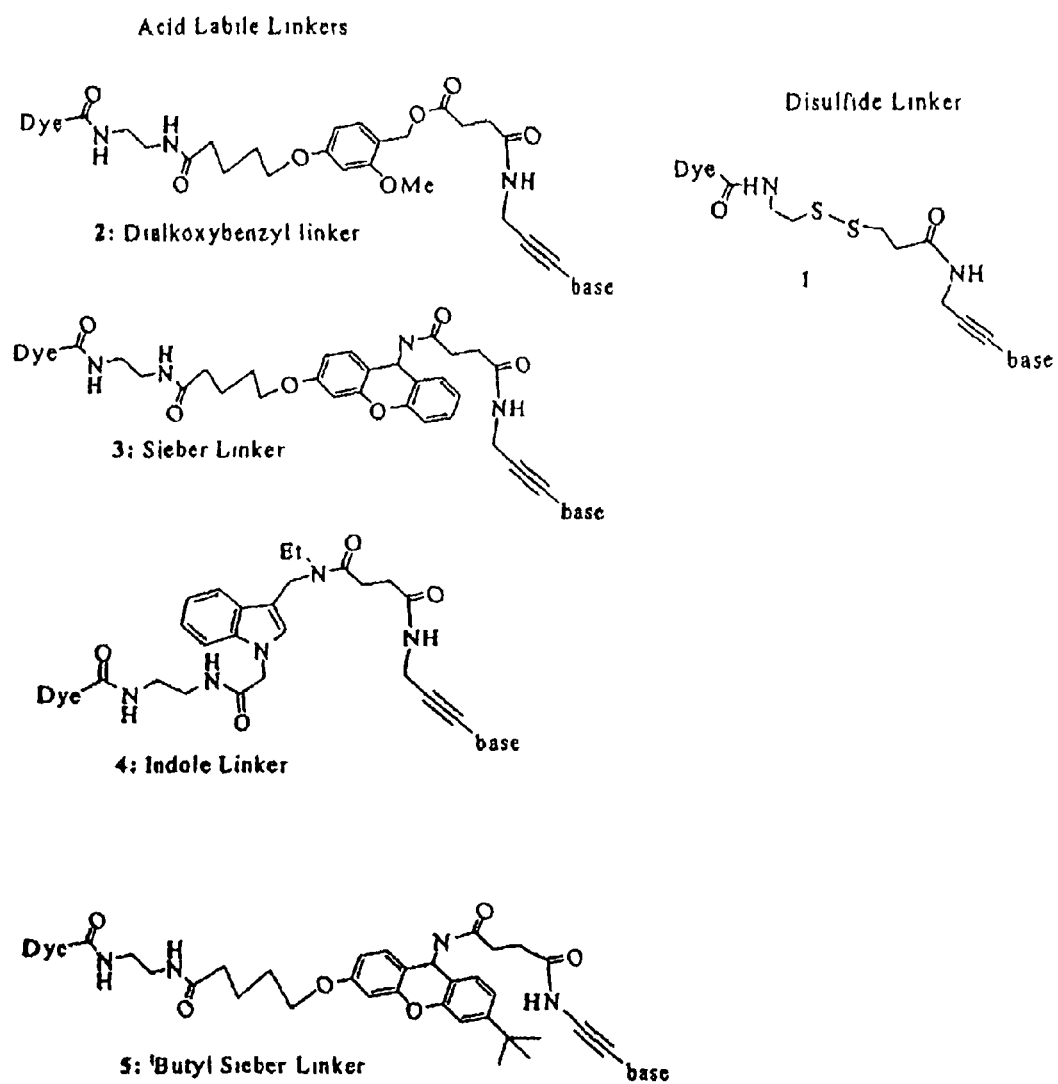
FIG. 2 shows some functional molecules useful in the invention, which include some cleavable linkers. In these structures, $R_1$ and $R_2$ may be the same or different, and can be H, OH, or any group which can be transformed into an OH group, including a carbonyl. $R_3$ represents one or more substituents independently selected from alkyl, alkoxyl, amino or halogen groups. Alternatively, cleavable linkers may be constructed from any labile functionality used on the 3'-block.
Figure 4:
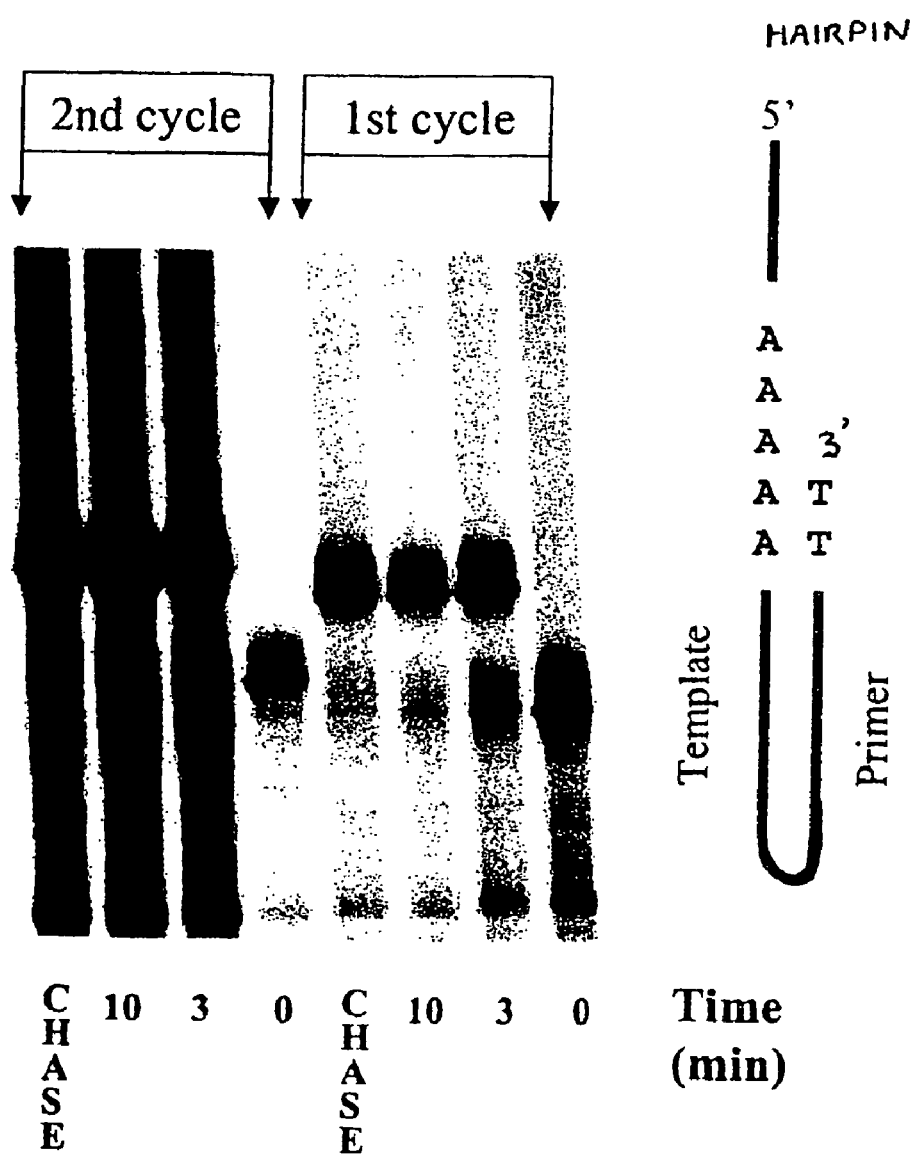
FIG. 4 shows two cycles of incorporation of a fully functional T nucleoside triphosphate against a poly A template

The nucleotide or nucleoside molecules of the invention each have a base that is linked to a detectable label via linkers that may be cleaved by contact with water-soluble phosphines or water-soluble transition metal-containing catalysts described in greater detail hereinafter. Preferably moiety "T" is hydrogen. The base can be a purine, or a pyrimidine. The base can be a deazapurine. The molecule can have a ribose or deoxyribose sugar moiety. The ribose or deoxyribose sugar can include a protecting group attached via the 2' or 3' oxygen atom. The protecting group can be removed to expose a 3'-OH. The molecule can be a deoxyribonucleotide triphosphate. The detectable label can be a fluorophore.

The invention also embraces oligonucleotides which comprise one or more nucleotides of the invention. Preferably, at least one nucleotide of the invention is present at a terminal position in such a oligonucleotide.

The linker may be attached to the 5-position in pyrimidines or the 7-position in purines or deazapurines. The characteristic feature of the nucleotides and nucleosides of the present invention is the amenability of the linkage to cleavage by certain water-soluble phosphines or phosphine-based transition metal catalysts. Since oligonucleotides are manipulated in aqueous solution, the advantages of this water-solubility are evident.

The cleavable linkages present in the nucleosides and nucleotides of the invention each comprise an allyl or azido group.

Where the linkers comprise an azide-containing group the linkers may contain a moiety of the formula:

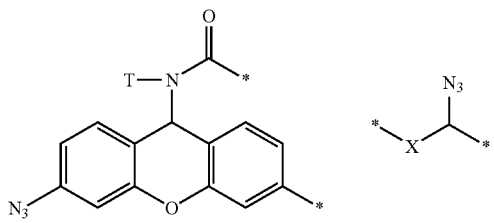

These moieties may be present in either orientation in the linker connecting the base of the nucleotide/nucleoside with the detectable label, that is to say either of the bonds shown terminating in asterisks in each moiety may be closer to the base (or the label) in each nucleotide or nucleoside than the other asterisk shown in each structure. Thus the invention embraces nucleotides and nucleoside having schematically the following structures (shown on the left-hand side) which may be reacted with the water-soluble phosphines (described in greater detail hereinafter) to generate the products shown on the right-hand side in which the azido-containing linker has been cleaved:

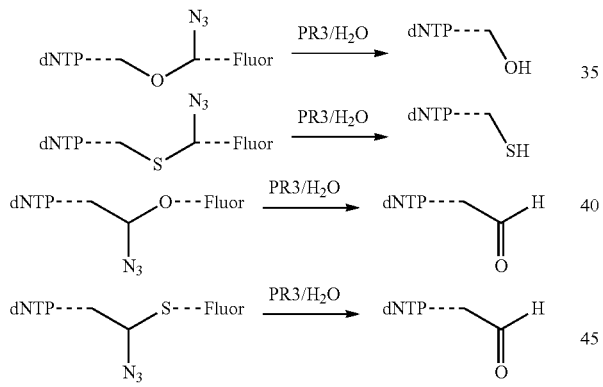

Whilst the connecting points * indicate the points at which the moieties are connected to the nucleotide or nucleoside, it will be appreciated that these points are generally the points at which the moiety is connected to the remainder of the linker. In other words, the moieties described herein that contain allyl or azido groups are generally part of, rather than exclusively constitute, the cleavable linker.

Where the moiety is of formula —X—CH(N$_3$)—, the nature of the substituents to either side of the moiety —X—CH(N3)- affects the stability of the moiety and thus the rate at which it is cleaved. For example, where the linkage contains a substituted aryl group attached to the moiety in which the substituents (indicated as "R" in the structures immediately below) are electron-withdrawing, this is manifested in the way in which the moiety cleaves. For example, electron-withdrawing groups, serve to stabilise the linkage particularly where X is O or S. This makes cleavage occur more slowly.

Shown below schematically are the outcomes of four cleavages of schematic nucleotide constructs and a further schematic representation of a preferred construct. The dotted lines connecting the "fluor", "dNTP" or R group to the benzene ring or the cleavable moieties indicate that substitution may be at any free position on the benzene ring and that further atoms (not shown) in the linker may be present between the cleavable motif shown and the nucleotide and detectable label which the linker connects:

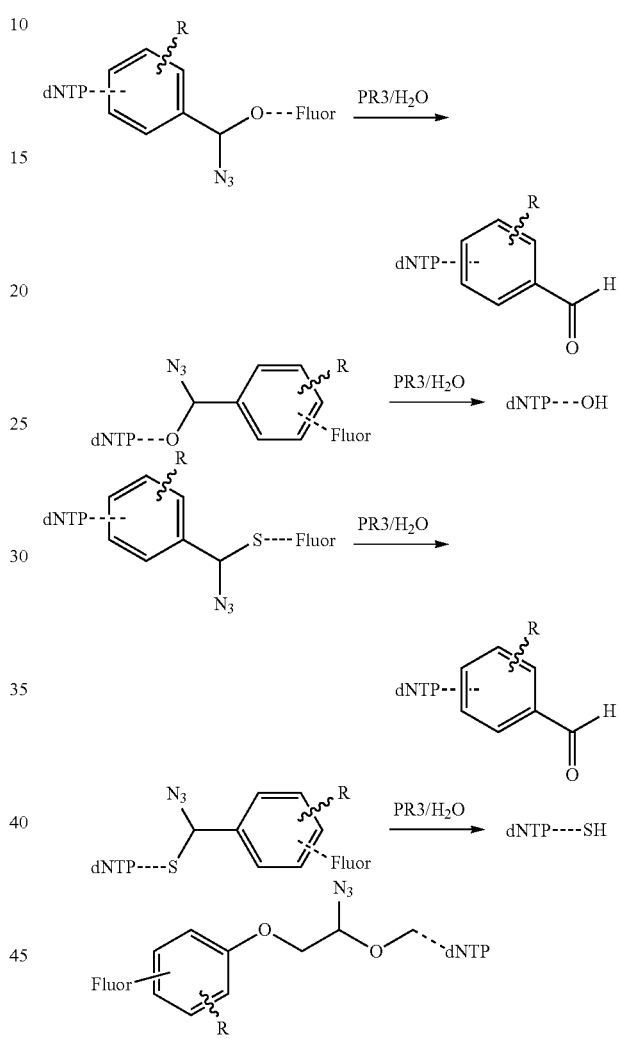

Where the azide-containing moieties are Sieber linkers, i.e. are of the formula

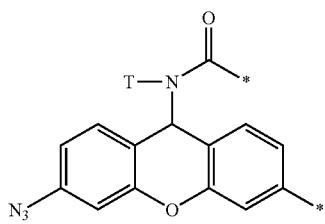

cleavage of the moiety takes place across the bond linking the central 6-membered ring of the tricycle to the amide such that a terminal amide group is left pendant to either the base or the fluorophore after cleavage.

It will be appreciated that the azide-containing Sieber linker moieties may contain one or more substituents which may be either electron-donating (examples include alkyl or alkoxy, e.g. $C_{1-6}$ alkyl or $C_{1-6}$ alkoxy groups) or electron-withdrawing groups (e.g. nitro, cyano, fluoro etc). Introduction of such substituents enables the skilled person to tailor the conditions under which cleavage may be effected.

Where the nucleotides comprise an azide group in the linker, this may be converted to the primary amine group with a thiol (in place of the phosphines), preferably a water-soluble thiol such as dithiothreitol (DTT).

Where the linkers comprise an allyl group, these may be of the formulae:

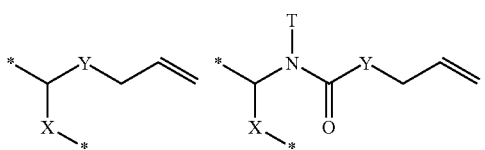

As with the azido-containing moieties discussed above, these linking moieties may be present in either orientation in the linker connecting the base of the nucleotide/nucleoside with the detectable label.

Where the linkages comprise allyl-containing moieties, these linkers may be cleaved with water-soluble transition metal catalysts formed from a transition metal and at least partially water-soluble ligands. In aqueous solution these form at least partially water-soluble transition metal complexes.

The transition metal species serves to remove the allyl group. Where the allyl group is part of carbamate, deallylation affords the corresponding carbamic acid. This spontaneously decarboxylates to afford a hemiaminal which hydrolyses so as to effect cleavage of the linker. Corresponding chemistries operate with the analogous thiocarbamate and carbonates so as to generate compounds containing moieties of structure *—C(NH$_2$)—X—*. These collapse by hydrolysing, again cleaving the linker.

By aqueous solution herein is meant a liquid comprising at least 20 vol %, preferably at least 50%, for example at least 75 vol %, particularly at least 95 vol % and especially greater than above 98 vol %, ideally 100 vol % of water as the continuous phase.

Transition metals of use in forming the catalysts described herein are preferably platinum, palladium, rhodium, ruthenium, osmium and iridium. Palladium is particularly preferred.

The transition metal, e.g. palladium, is conveniently introduced as a salt, e.g. as a halide. Mixed salts such as $Na_2PdCl_4$ may also be used. Other appropriate salts and compounds will be readily determined by the skilled person and are commercially available, e.g. from Aldrich Chemical Company.

Suitable phosphines are any phosphine or mixed nitrogen-phosphine ligands known to those skilled in the art, characterised in that the ligands are derivatised so as to render them water-soluble, e.g. by introducing one or more sulfonate, amine, hydroxyl (preferably a plurality of hydroxyl) or carboxylate residues. Where amine residues are present, formation of amine salts may assist the solublisation of the ligand and thus the metal-allyl complex. Examples of appropriate ligands are triaryl phosphines, e.g. triphenyl phosphine, derivatised so as to make them water-soluble. Also preferred are trialkyl phosphines, e.g. tri-$C_{1-6}$-alkyl phosphines such as triethyl phosphines; such trialkyl phosphines are likewise derivatised so as to make them water-soluble. Sulfonate-containing and carboxylate-containing phosphines are particularly preferred; an example of the former 3,3',3''-phosphinidynetris(benzenesulfonic acid) which is commercially available from Aldrich Chemical Company as the trisodium salt; and a preferred example of the latter is tris(2-carboxyethyl)phosphine which is available from Aldrich as the hydrochloride salt. The derivatised water-soluble phosphines and nitrogen-containing phosphines described herein may be used as their salts (e.g. as the hydrochloride or sodium salts) or, for example, in the case of the sulfonic and carboxylic acid-containing phosphines described herein, as the free acids. Thus 3,3',3''-phosphinidynetris (benzenesulfonic acid) and tris(2-carboxyethyl)phosphines may be introduced either as the triacids or the trisodium salts. Other appropriate salts will be evident to those skilled in the art. The existence in salt form is not particularly important provided the phosphines are soluble in aqueous solution.

Other phosphines which may be used include the following:

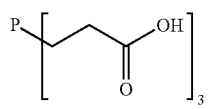

as the hydrochloride salt, neutral compound and the trisodium salt

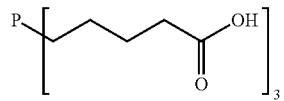

as the hydrochloride salt, neutral compound and the trisodium salt

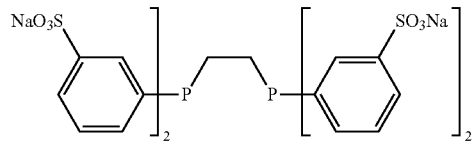

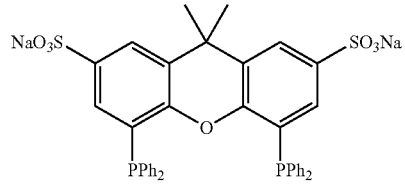

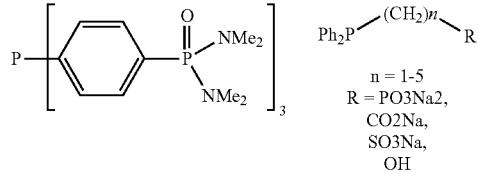

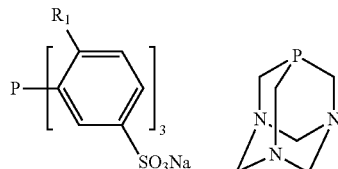 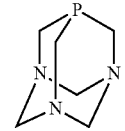

R1 = OMe, CO2H, CO2Na

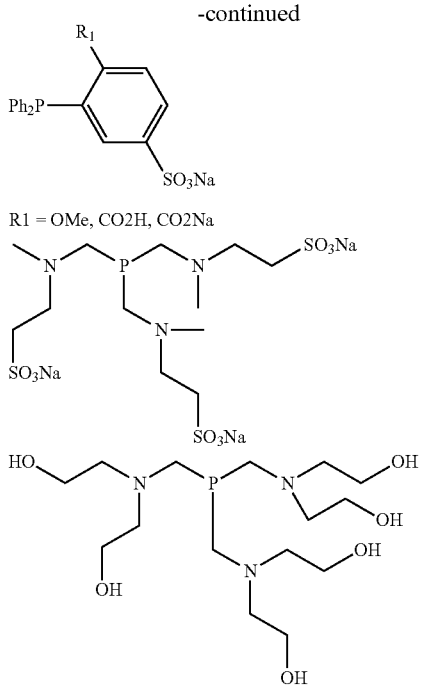

The skilled person will be aware that the atoms chelated to the transition metal in the water soluble complex may be part of mono- or polydentate ligands. Some such polydentate ligands are shown above. Whilst monodentate ligands are preferred, the invention thus also embraces methods which use water-soluble bi-, tri-, tetra-, penta- and hexadentate water-soluble phosphine and water-soluble nitrogen-containing phosphine ligands.

As noted earlier, the aqueous solution in which deprotection is effected need not be 100% (as the continuous phase). However, substantially pure water (e.g. at least 98 vol % and preferably about 100 vol %) is preferred. Cosolvents are generally not required. Generally, nucleotides and nucleosides are readily soluble in water (e.g. pure water) in which the linkage cleavage described herein may be effected. If desirable, one or more water-miscible cosolvents may be employed. Appropriate solvents include acetonitrile or dimethylsulfoxide, methanol, ethanol and acetone, methanol being preferred. Less preferred solvents include tetrahydrofuran (THF) and dioxane.

In the methods of cleaving allyl-containing moieties according to the invention, a soluble metal complex is formed comprising a transition metal and one or more water-soluble phosphine ligands (including water-soluble nitrogen-containing phosphine ligands). More than one type of water-soluble phosphine/nitrogen-containing phosphine ligand may be used in any given reaction although generally only one type of these classes of ligand will be used in any given catalyst. The quantity of transition metal, e.g. palladium, may be less than 1 mol % (calculated relative to the number of moles of linkage to be cleaved). Advantageously the amount of catalyst may be much less than 1 mol %, e.g. <0.50 mol %, preferably <0.10 mol %, particularly <0.05 mol %. Even lower quantities of metal may be used, for example <0.03 or even <0.01 mol %. As those skilled in the art will be aware, however, as quantity of catalyst is reduced, so too is the speed of the reaction. The skilled person will be able to judge, in any instance, an appropriate quantity of transition metal and thus catalyst suitable for any particular reaction.

In contrast to the amount of metal required in forming the active catalyst, the quantity of water-soluble phosphine-containing ligand(s) used is preferably be greater than 1 molar equivalent (again calculated relative to the number of moles of linkage to be cleaved). Preferably greater than 4, e.g. greater than 6, for example 8-12 molar equivalents of ligand may be used. Even higher quantities of ligand e.g. >20 mole equivalents may be used if desired.

The skilled person will be able to determine the quantity of ligand best suited to any individual reaction.

Where the linkage contains an azide group, the presence of a transition metal is not necessary to effect cleavage. Thus cleavage of such linkers may be effected in the presence only of the phosphines discussed herein; these may be present in the methods of the invention as water-soluble salts, such as those discussed herein.

As is known in the art, a "nucleotide" consists of a nitrogenous base, a sugar, and one or more phosphate groups. In RNA, the sugar is a ribose, and in DNA is a deoxyribose, i.e., a sugar lacking a hydroxyl group that is present in ribose. The nitrogenous base is a derivative of purine or pyrimidine. The purines are adenosine (A) and guanidine (G), and the pyrimidines are cytidine (C) and thymidine (T) (or in the context of RNA, uracil (U)). The C-1 atom of deoxyribose is bonded to N-1 of a pyrimidine or N-9 of a purine. A nucleotide is also a phosphate ester of a nucleoside, with esterification occurring on the hydroxyl group attached to C-5 of the sugar. Nucleotides are usually mono-, di- or triphosphates.

A "nucleoside" is structurally similar to a nucleotide, but is missing the phosphate moieties. An example of a nucleoside analog would be one in which the label is linked to the base and there is no phosphate group attached to the sugar molecule.

Although the base is usually referred to as a purine or pyrimidine, the skilled person will appreciate that derivatives and analogs are available which do not alter the capability of the nucleotide or nucleoside to undergo Watson-Crick base pairing. "Derivative" or "analog" means a compound or molecule whose core structure is the same as, or closely resembles that of, a parent compound, but which has a chemical or physical modification, such as a different or additional side group, which allows the derivative nucleotide or nucleoside to be linked to another molecule. For example, the base can be a deazapurine.

The modified nucleotides or nucleotides disclosed and claimed herein are examples of such derivatives or analogues with the addition of detectable labels connected to the bases by the cleavable allyl- or azido-containing linkers described herein. Thus the terms nucleotides and nucleosides as used herein will be understood to embrace such modified nucleosides and nucleotides.

The derivatives should be capable of undergoing Watson-Crick pairing. "Derivative" and "analogue" also mean a synthetic nucleotide or nucleoside derivative having modified base moieties and/or modified sugar moieties. Such derivatives and analogs are discussed in, e.g., Scheit, Nucleotide Analogs (John Wiley & Son, 1980) and Uhlman et al., Chemical Reviews 90:543-584, 1990. Nucleotide analogs can also comprise modified phosphodiester linkages, including phosphorothioate, phosphorodithioate, alkyl-phosphonate, phosphoranilidate and phosphoramidate linkages. The analogs should be capable of undergoing Watson-Crick base pairing. "Derivative", "analog" and "modified" as used herein, may be used interchangeably, and are encompassed by the terms "nucleotide" and "nucleoside" defined herein.

The methods of the present invention make use of conventional detectable labels. Detection can be carried out by any suitable method, including fluorescence spectroscopy or by other optical means. The preferred label is a fluorophore, which, after absorption of energy, emits radiation at a defined wavelength. Many suitable fluorescent labels are known. For example, Welch et al. (*Chem. Eur. J.* 5(3):951-960, 1999) discloses dansyl-functionalised fluorescent moieties that can be used in the present invention. Zhu et al. (*Cytometry* 28:206-211, 1997) describes the use of the fluorescent labels Cy3 and Cy5, which can also be used in the present invention. Labels suitable for use are also disclosed in Prober et al. (*Science* 238:336-341, 1987); Connell et al. (*BioTechniques* 5(4):342-384, 1987), Ansorge et al. (*Nucl. Acids Res.* 15(11): 4593-4602, 1987) and Smith et al. (*Nature* 321:674, 1986). Other commercially available fluorescent labels include, but are not limited to, fluorescein, rhodamine (including TMR, Texas red and Rox), alexa, bodipy, acridine, coumarin, pyrene, benzanthracene and the cyanins.

Multiple labels can also be used in the invention. For example, bi-fluorophore FRET cassettes (*Tet. Letts.* 46:8867-8871, 2000) are well known in the art and can be utilised in the present invention. Multi-fluor dendrimeric systems (*J. Amer. Chem. Soc.* 123:8101-8108, 2001) can also be used.

Although fluorescent labels are preferred, other forms of detectable labels will be apparent as useful to those of ordinary skill. For example, microparticles, including quantum dots (Empodocles, et al., *Nature* 399:126-130, 1999), gold nanoparticles (Reichert et al., *Anal. Chem.* 72:6025-6029, 2000), microbeads (Lacoste et al., *Proc. Natl. Acad. Sci USA* 97(17):9461-9466, 2000), and tags detectable by mass spectrometry can all be used.

Multi-component labels can also be used in the invention. A multi-component label is one which is dependent on the interaction with a further compound for detection. The most common multi-component label used in biology is the biotin-streptavidin system. Biotin is used as the label attached to the nucleotide base. Streptavidin is then added separately to enable detection to occur. Other multi-component systems are available. For example, dinitrophenol has a commercially available fluorescent antibody that can be used for detection.

The label (or label and linker construct) can be of a size or structure sufficient to act as a block to the incorporation of a further nucleotide onto the nucleotide of the invention. This permits controlled polymerization to be carried out. The block can be due to steric hindrance, or can be due to a combination of size, charge and structure.

The invention will be further described primarily with reference to nucleotides. However, unless indicated otherwise, the references herein to nucleotides are also intended to be applicable to nucleosides. The invention will also be further described with reference to DNA, although the description will also be applicable to RNA, PNA, and other nucleic acids, unless otherwise indicated.

The modified nucleotides of the invention use a cleavable linker to attach the label to the nucleotide. The use of a cleavable linker ensures that the label can, if required, be removed after detection, avoiding any interfering signal with any labelled nucleotide incorporated subsequently.

The use of the term "cleavable linker" is not meant to imply that the whole linker is required to be removed from the nucleotide base. The cleavage site can be located at a position on the linker that ensures that part of the linker remains attached to the nucleotide base after cleavage.

The linker can be attached at any position on the nucleotide base provided that Watson-Crick base pairing can still be carried out. In the context of purine bases, it is preferred if the linker is attached via the 7-position of the purine or the preferred deazapurine analogue, via an 8-modified purine, via an N-6 modified adenosine or an N-2 modified guanine. For pyrimidines, attachment is preferably via the 5-position on cytidine, thymidine or uracil and the N-4 position on cytosine. Suitable nucleotide structures are shown in FIG. 1. For each structure in FIG. 1, X can be H, phosphate, diphosphate or triphosphate. $R_1$ and $R_2$ can be the same or different, and can be selected from H, OH, or any group which can be transformed into an OH, including, but not limited to, a carbonyl.

Suitable linkers comprise the azide- and allyl-containing moieties discussed earlier. However, in addition to these cleavable moieties, other cleavable motifs may of course also be present in the linkers. Referring to FIG. 2, examples of these include, but are not limited to, disulfide linkers (1), acid labile moieties (2, 3, 4 and 5; including dialkoxybenzyl moieties (e.g., 2), Sieber linkers (e.g., 3), indole moieties (e.g., 4), t-butyl Sieber moieties (e.g., 5)), electrophilically cleavable moieties, nucleophilically cleavable moieties, photocleavable moieties; cleavage under reductive conditions, oxidative conditions, cleavage via use of safety-catch moieties, and cleavage by elimination mechanisms. Examples of such moieties are described in WO03/048387.

As well as the moiety cleavable by water-soluble phosphines or transition metal-based catalysts described herein, the cleavable linkages may also comprise a spacer unit. The spacer distances the nucleotide base from the cleavage site or label. The length of the moiety is unimportant provided that the label is held a sufficient distance from the nucleotide so as not to interfere with any interaction between the nucleotide and an enzyme.

Such spacing groups may contain one or more arylene, e.g. phenylene, groups in the chain (i.e. a moiety —Ar— where the phenyl ring is part of the linker by way of its 1,4, 1,3 or 1,2-disposed carbon atoms). The phenyl ring may be substituted at its non-bonded position with one or more substituents such as alkyl, hydroxyl, alkyloxy, halide, nitro, carboxyl or cyano and the like, particularly electron-withdrawing groups, which electron-withdrawing is either by induction or resonance. An example of an electron-withdrawing group by resonance is nitro; a group which acts through induction is fluoro. The skilled person will be aware of other appropriate electron-withdrawing groups. The linkage in the R' group may also include moieties such a —O—, —$S(O)_q$—, wherein $q$ is 0, 1 or 2 or NH or Nalkyl.

The modified nucleotides can also comprise additional groups or modifications to the sugar group. For example, a dideoxyribose derivative, lacking both hydroxyl groups on the ribose ring structure (at the 2' and 3' positions), can be prepared and used as a block to further nucleotide incorporation on a growing oligonucleotide strand. The protecting group is intended to prevent nucleotide incorporation onto a nascent polynucleotide strand, and can be removed under defined conditions to allow polymerisation to occur. In contrast to the prior art, there need be no detectable label attached at the ribose 3' position. This allows that steric hindrance with the polymerase enzyme to be reduced, while still allowing control of incorporation using the protecting group.

The skilled person will appreciate how to attach a suitable protecting group to the ribose ring to block interactions with the 3'-OH. The protecting group can be attached directly at the 3' position, or can be attached at the 2' position (the protecting group being of sufficient size or charge to block interactions at the 3' position). Alternatively, the protecting group can be attached at both the 3' and 2' positions, and can be cleaved to expose the 3'OH group.

Suitable protecting groups will be apparent to the skilled person, and can be formed from any suitable protecting group disclosed in "Protective Groups in Organic Synthesis", T. W.

Greene and P. G. M. Wuts, 3rd Ed., Wiley Interscience, New York. The protecting group should be removable (or modifiable) to produce a 3' OH group. The process used to obtain the 3' OH group can be any suitable chemical or enzymic reaction.

Preferably, the blocking, or protecting group is an allyl group or a group of the structure

wherein Z is any of —C(R')$_2$—O—R", —C(R')$_2$—N(R")$_2$, —C(R")$_2$—N(H)R", —C(R')$_2$—S—R" and —C(R')$_2$—F, wherein each R" is or is part of a removable protecting group;

each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group; or (R')$_2$ represents an alkylidene group of formula =C(R''')$_2$ wherein each R''' may be the same or different and is selected from the group comprising hydrogen and halogen atoms and alkyl groups; and wherein said molecule may be reacted to yield an intermediate in which each R" is exchanged for H or, where Z is —C(R')$_2$—F, the F is exchanged for OH, SH or NH$_2$, preferably OH, which intermediate dissociates under aqueous conditions to afford a molecule with a free 3'H;

with the proviso that where Z is —C(R')$_2$—S—R", both R' groups are not H.

Where the blocking group is an allyl group, it may be introduced into the 3'-position using standard literature procedures such as that used by Metzker (*Nucleic Acids Research*, 22(20):4259-4267, 1994).

The intermediates produced advantageously spontaneously dissociate under aqueous conditions back to the natural 3' hydroxy structure, which permits further incorporation of another nucleotide. Any appropriate protecting group may be used. Preferably, Z is of formula —C(R')$_2$—O—R", —C(R')$_2$—N(R")$_2$, —C(R')$_2$—N(H)R" and —C(R')$_2$—SR". Particularly preferably, Z is of the formula —C(R')$_2$—O—R", —C(R')$_2$—N(R")$_2$, and —C(R')$_2$—SR". R" may be a benzyl group or a substituted benzyl group.

One example of groups of structure —O—Z wherein Z is —C(R')$_2$—N(R")$_2$ are those in which —N(R")$_2$ is azido (—N$_3$). One preferred such example is azidomethyl wherein each R' is H. Alternatively, R' in Z groups of formula —C(R')$_2$—N$_3$ and other Z groups may be any of the other groups discussed herein. Examples of typical R' groups include C$_{1-6}$ alkyl, particularly methyl and ethyl, and the following (in which each structure shows the bond which connects the R' moiety to the carbon atom to which it is attached in the Z groups; the asterisks (*) indicate the points of attachment):

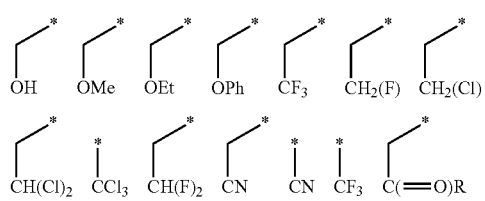

-continued

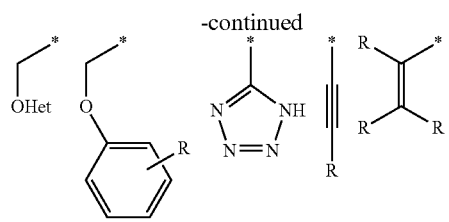

(wherein each R is an optionally substituted C$_{1-10}$ alkyl group, an optionally substituted alkoxy group, a halogen atom or functional group such as hydroxyl, amino, cyano, nitro, carboxyl and the like) and "Het" is a heterocyclic (which may for example be a heteroaryl group). These R' groups shown above are preferred where the other R' group is the same as the first or is hydrogen. Preferred Z groups are of formula C(R')$_2$N$_3$ in which the R' groups are selected from the structures given above and hydrogen; or in which (R')$_2$ represents an alkylidene group of formula =C(R''')$_2$, e.g. =C(Me)$_2$.

Where molecules contain Z groups of formula C(R')$_2$N$_3$, the azido group may be converted to amino by contacting such molecules with the phosphine or nitrogen-containing phosphines ligands described in detail in connection with the transition metal complexes which serve to cleave the allyl groups from compounds of formula PN—O-allyl, formula R—O-allyl, R$_2$N(allyl), RNH(allyl), RN(allyl)$_2$ and R—S-allyl. When transforming azido to amino, however, no transition metal is necessary. Alternatively; the azido group in Z groups of formula c(R')$_2$N$_3$ may be converted to amino by contacting such molecules with the thiols, in particular water-soluble thiols such as dithiothreitol (DTT).

The labile linker may, and preferably does, consist of functionality cleavable under identical conditions to the block. This makes the deprotection process more efficient since only a single treatment will be required to cleave both the label and the block. For example, where the linkage contains an allyl moiety as discussed and claimed herein and the blocking group is an allyl group, both linkage and blocking group will be cleavable under identical conditions. Similarly, if the linkage contains an azido moiety as discussed and claimed herein and the blocking group comprises an azido moiety, e.g. is of formula Z wherein R" is N$_3$ as discussed hereinbefore, both linkage and blocking group will be cleavable under identical conditions. The blocking group may of course be deprotected under entirely different chemical conditions to those required to cleave the linker.

The term "alkyl" covers both straight chain and branched chain alkyl groups. Unless the context indicates otherwise, the term "alkyl" refers to groups having 1 to 10 carbon atoms, for example 1 to 8 carbon atoms, and typically from 1 to 6 carbon atoms, for example from 1 to 4 carbon atoms. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers.

Examples of cycloalkyl groups are those having from 3 to 10 ring atoms, particular examples including those derived from cyclopropane, cyclobutane, cyclopentane, cyclohexane and cycloheptane, bicycloheptane and decalin.

Where alkyl (including cycloalkyl) groups are substituted, particularly where these form either both of the R' groups of the molecules of the invention, examples of appropriate substituents include halogen substituents or functional groups such as hydroxyl, amino, cyano, nitro, carboxyl and the like.

Such groups may also be substituents, where appropriate, of the other R' groups in the molecules of the invention.

Examples of alkenyl groups include, but are not limited to, ethenyl(vinyl), 1-propenyl, 2-propenyl (allyl), isopropenyl, butenyl, buta-1,4-dienyl, pentenyl, and hexenyl.

Examples of cycloalkenyl groups include, but are not limited to, cyclopropenyl, cyclobutenyl, cyclopentenyl, cyclopentadienyl and cyclohexenyl.

The term alkoxy refers to $C_{1-6}$ alkoxy unless otherwise indicated: —OR, wherein R is a $C_{1-6}$alkyl group. Examples of $C_{1-6}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

The term "halogen" as used herein includes fluorine, chlorine, bromine and iodine.

The nucleotide molecules of the present invention are suitable for use in many different methods where the detection of nucleotides is required.

DNA sequencing methods, such as those outlined in U.S. Pat. No. 5,302,509 can be carried out using the nucleotide.

Preferably the blocked and labelled modified nucleotide constructs of the nucleotide bases A, T, C and G are recognised as substrates by the same polymerase enzyme.

In the methods described herein, each of the nucleotides can be brought into contact with the target sequentially, with removal of non-incorporated nucleotides prior to addition of the next nucleotide, where detection and removal of the label and the blocking group, if present is carried out either after addition of each nucleotide, or after addition of all four nucleotides.

In the methods, all of the nucleotides can be brought into contact with the target simultaneously, i.e., a composition comprising all of the different nucleotides is brought into contact with the target, and non-incorporated nucleotides are removed prior to detection and subsequent to removal of the label and the blocking group, if present.

The four nucleotides, one of which will be complementary to the first unpaired base in the target polynucleotide, may be brought into contact with the target sequentially, optionally with removal of non-incorporated nucleotides prior to addition of the next nucleotide. Determination of the success of the incorporation may be carried out either after provision of each nucleotide, or after the addition of all of the nucleotides added. If it is determined after addition of fewer than four nucleotides that one has been incorporated, it is not necessary to provide further nucleotides in order to detect the nucleotides complementary to the incorporated nucleotide.

Alternatively, all of the nucleotides can be brought into contact with the target simultaneously, i.e., a composition comprising all of the different nucleotide (i.e. A, T, C and G or A, U, C and G) is brought into contact with the target, and non-incorporated nucleotides removed prior to detection and removal of the label(s). The methods involving sequential addition of nucleotides may comprise a first substep and optionally one or more subsequent substeps. In the first substep a composition comprising one, two or three of the four possible nucleotides is provided, i.e. brought into contact with, the target. Thereafter any unincorporated nucleotides may be removed and a detecting step may be conducted to determine whether one of the nucleotides has been incorporated. If one has been incorporated, the cleavage of the linker may be effected and, if necessary, a terminal amide functionality introduced thereafter to the pendant arm. In this way the identity of a nucleotide in the target polynucleotide may be determined. The nascent polynucleotide may then be extended to determine the identity of the next unpaired nucleotide in the target oligonucleotide.

If the first substep above does not lead to incorporation of a nucleotide, or if this is not known, since the presence of incorporated nucleotides is not sought immediately after the first substep, one or more subsequent substeps may be conducted in which some or all of those nucleotides not provided in the first substep are provided either, as appropriate, simultaneously or subsequently. Thereafter any unincorporated nucleotides may be removed and a detecting step conducted to determine whether one of the classes of nucleotide has been incorporated. If one has been incorporated, cleavage of the linker may be effected, and if necessary as an additional step or steps, terminal amide functionality introduced to the pendant arm. In this way the identity of a nucleotide in the target polynucleotide may be determined. The nascent polynucleotide may then be extended to determine the identity of the next unpaired nucleotide in the target oligonucleotide. If necessary, a third and optionally a fourth substep may be effected in a similar manner to the second substep. Obviously, once four substeps have been effected, all four possible nucleotides will have been provided and one will have been incorporated.

It is desirable to determine whether a type or class of nucleotide has been incorporated after any particular combination comprising one, two or three nucleotides has been provided. In this way the unnecessary cost and time expended in providing the other nucleotide(s) is obviated. This is not a required feature of the invention, however.

It is also desirable, where the method for sequencing comprises one or more substeps, to remove any unincorporated nucleotides before further nucleotide are provided. Again, this is not a required feature of the invention. Obviously, it is necessary that at least some and preferably as many as practicable of the unincorporated nucleotides are removed prior to the detection of the incorporated nucleotide.

A method for determining the sequence of a target polynucleotide can be carried out by contacting the target polynucleotide separately with the different nucleotides to form the complement to that of the target polynucleotide, and detecting the incorporation of the nucleotides. Such a method makes use of polymerisation, whereby a polymerase enzyme extends the complementary strand by incorporating the correct nucleotide complementary to that on the target. The polymerisation reaction also requires a specific primer to initiate polymerisation.

For each cycle, the incorporation of the modified nucleotide is carried out by the polymerase enzyme, and the incorporation event is then determined. Many different polymerase enzymes exist, and it will be evident to the person of ordinary skill which is most appropriate to use. Preferred enzymes include DNA polymerase I, the Klenow fragment, DNA polymerase III, T4 or T7 DNA polymerase, Taq polymerase or Vent polymerase. Polymerases engineered to have specific properties can also be used. Preferably, the molecule is incorporated by a polymerase and particularly from *Thermococcus* sp., such as 9°N. Even more preferably, the polymerase is a mutant 9°N A485L and even more preferably is a double mutant Y409V and A485L. An example of one such preferred enzyme is *Thermococcus* sp. 9°N exo-Y409V A485L available from New England Biolabs. Examples of such appropriate polymerases are disclosed in *Proc. Natl. Acad. Sci.* USA; 1996(93), pp 5281-5285, *Nucleic Acids Research,* 1999(27), pp 2454-2553 and *Acids Research,* 2002(30), pp 605-613.

Those skilled in the art will be aware of the utility of dideoxynucleoside triphosphates in so-called Sanger sequencing methods, and related protocols (Sanger-type), which rely upon randomised chain-termination at a particular type of nucleotide. An example of a Sanger-type sequencing protocol is the BASS method described by Metzker (infra). Other Sanger-type sequencing methods will be known to those skilled in the art.

Sanger and Sanger-type methods generally operate by the conducting of an experiment in which eight types of nucleotides are provided, four of which contain a 3'OH group; and four of which omit the OH group and which are labeled differently from each other. The nucleotides used which omit the 3'OH group—dideoxy nucleotides—are conventially abbreviated to ddNTPs. As is known by the skilled person, since the ddNTPs are labeled differently, by determining the positions of the terminal nucleotides incorporated, and combining this information, the sequence of the target oligonucleotide may be determined.

It will be recognized that the nucleotides of the present invention in which the 3'OH group is either absent or blocked may be of utility in Sanger methods and related protocols since the same effect achieved by using ddNTPs may be achieved by using 3'-OH blocking groups: both prevent incorporation of subsequent nucleotides.

The use of the nucleotides according to the present invention in Sanger and Sanger-type sequencing methods form a still further aspect of this invention. Viewed from this aspect, the invention provides the use of such nucleotides in a Sanger or a Sanger-type sequencing method.

The sequencing methods are preferably carried out with the target polynucleotide arrayed on a solid support. Multiple target polynucleotides can be immobilised on the solid support through linker molecules, or can be attached to particles, e.g., microspheres, which can also be attached to a solid support material.

The polynucleotides can be attached to the solid support by a number of means, including the use of biotin-avidin interactions. Methods for immobilizing polynucleotides on a solid support are well known in the art, and include lithographic techniques and "spotting" individual polynucleotides in defined positions on a solid support. Suitable solid supports are known in the art, and include glass slides and beads, ceramic and silicon surfaces and plastic materials. The support is usually a flat surface although microscopic beads (microspheres) can also be used and can in turn be attached to another solid support by known means. The microspheres can be of any suitable size, typically in the range of from 10 nm to 100 nm in diameter. In a preferred embodiment, the polynucleotides are attached directly onto a planar surface, preferably a planar glass surface. Attachment will preferably be by means of a covalent linkage. Preferably, the arrays that are used are single molecule arrays that comprise polynucleotides in distinct optically resolvable areas, e.g., as disclosed in International App. No. WO 00/06770.

The sequencing method can be carried out on both single polynucleotide molecule and multi-polynucleotide molecule arrays, i.e., arrays of distinct individual polynucleotide molecules and arrays of distinct regions comprising multiple copies of one individual polynucleotide molecule. Single molecule arrays allow each individual polynucleotide to be resolved separately. The use of single molecule arrays is preferred. Sequencing single molecule arrays non-destructively allows a spatially addressable array to be formed.

The method makes use of the polymerisation reaction to generate the complementary sequence of the target. Conditions compatible with polymerization reactions will be apparent to the skilled person.

To carry out the polymerase reaction it will usually be necessary to first anneal a primer sequence to the target polynucleotide, the primer sequence being recognised by the polymerase enzyme and acting as an initiation site for the subsequent extension of the complementary strand. The primer sequence may be added as a separate component with respect to the target polynucleotide. Alternatively, the primer and the target polynucleotide may each be part of one single stranded molecule, with the primer portion forming an intramolecular duplex with a part of the target, i.e., a hairpin loop structure. This structure may be immobilised to the solid support at any point on the molecule. Other conditions necessary for carrying out the polymerase reaction, including temperature, pH, buffer compositions etc., will be apparent to those skilled in the art.

The modified nucleotides of the invention are then brought into contact with the target polynucleotide, to allow polymerisation to occur. The nucleotides may be added sequentially, i.e., separate addition of each nucleotide type (A, T, G or C), or added together. If they are added together, it is preferable for each nucleotide type to be labelled with a different label.

This polymerisation step is allowed to proceed for a time sufficient to allow incorporation of a nucleotide.

Nucleotides that are not incorporated are then removed, for example, by subjecting the array to a washing step, and detection of the incorporated labels may then be carried out.

Detection may be by conventional means, for example if the label is a fluorescent moiety, detection of an incorporated base may be carried out by using a confocal scanning microscope to scan the surface of the array with a laser, to image a fluorophore bound directly to the incorporated base. Alternatively, a sensitive 2-D detector, such as a charge-coupled detector (CCD), can be used to visualise the individual signals generated. However, other techniques such as scanning near-field optical microscopy (SNOM) are available and may be used when imaging dense arrays. For example, using SNOM, individual polynucleotides may be distinguished when separated by a distance of less than 100 nm, e.g., 10 nm to 10 μm. For a description of scanning near-field optical microscopy, see Moyer et al., *Laser Focus World* 29:10, 1993. Suitable apparatus used for imaging polynucleotide arrays are known and the technical set-up will be apparent to the skilled person.

After detection, the label may be removed using suitable conditions that cleave the linker.

The use of the modified nucleotides is not limited to DNA sequencing techniques, and other techniques, including polynucleotide synthesis, DNA hybridisation assays and single nucleotide polymorphism studies, may also be carried out using nucleotides of the invention. Any technique that involves the interaction between a nucleotide and an enzyme may make use of the molecules of the invention. For example, the molecule may be used as a substrate for a reverse transcriptase or terminal transferase enzyme.

Suitable nucleotide structures are described in the following non-limiting Examples and are shown in the accompanying drawings.

3-(2,2-Diethoxy-ethoxy)-benzoic acid ethyl ester

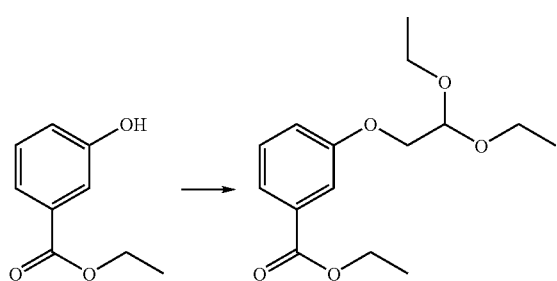

2-Bromoacetaldehyde diethyl acetal (3 ml, 20 mmol), ethyl-3-hydroxy-benzoate (1.66 g, 10 mmol), potassium carbonate (2.76 g, 20 mmol) and sodium iodide (0.298 g, 2 mmol) were heated at 120° C. in dimethyl formamide (DMF) (15 ml) for 17 hrs. Another batch of 2-bromoacetaldehyde diethyl acetal (3 ml, 20 mmol) was added and the reaction mixture was heated at 120° C. for another 24 hrs. The reaction was cooled to room temperature and all the solvents were evaporated under reduced pressure. The residues were partitioned between dichloromethane (DCM) (200 ml) and water (200 ml). The DCM layer was separated and the aqueous layer was back-extracted with DCM (2×100 ml). All the DCM extracts were combined, dried over MgSO$_4$ and evaporated under reduced pressure. The residue was purified by a column chromatography (4×20 cm). The product was eluted with 100% DCM and the title compound was obtained as a colourless oil (2.21 g, 78.3%).

$^1$HNMR [CDCl$_3$]: 7.58 (1H, Ar—H, d J 7.7), 7.51 (1H, Ar—H, dd, J 2.4 and 1.5), 7.27 (1H, Ar—H, t, J 8.0), 7.05 (1H, Ar—H, dd, J 7.9 and 2.3), 4.79 (1H, CH, t, J 5.2), 4.20 (2H, OCH$_2$, q, J 7.2), 3.99 (2H, ArOCH$_2$, d, J 5.2), 3.75-3.65 (2H, OCH$_2$, m), 3.63-3.53 (2H, OCH$_2$, m), 1.33 (3H, CH$_3$, t, J 7.2) and 1.19 (6H, CH$_3$, t, J 7.1).

3-(2-Azido-2-ethoxy-ethoxy)-benzoic acid ethyl ester

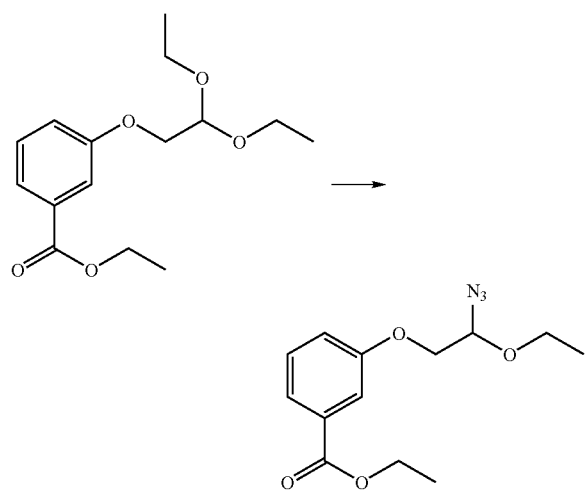

To a mixture of 3-(2,2-diethoxy-ethoxy)-benzoic acid ethyl ester (1.128 g, 4 mmol) and azidotrimethylsilane (0.584 ml, 4.4 mmol) was added SnCl$_4$ (40 μl) at room temperature. After 1 hr, the precipitates were filtered off and the filtrate was evaporated under reduced pressure. The residue was dissolved in methanol, after 10 minutes, solvent was removed under reduced pressure. The residue was purified by a column chromatography (3×20 cm). The product was eluted with 10% petroleum ether (60-80° C.) in DCM. The title compound was obtained as a colourless oil (0.909 g, 81.5%).

$^1$HNMR [CDCl$_3$]: 7.51 (1H, Ar—H, d J 7.7), 7.41 (1H, Ar—H, dd, J 2.6 and 1.5), 7.19 (1H, Ar—H, t, J 7.9), 6.96 (1H, Ar—H, ddd, J 8.2, 2.7 and 0.9), 4.63 (1H, CHN$_3$, t, J 5.1), 4.20 (2H, OCH$_2$, q, J 7.2), 4.05-3.90 (2H, ArOCH$_2$, m), 3.80-3.78 (1H, OCH$_2$, H$_a$, m), 3.55-3.47 (1H, OCH$_2$, H$_b$, m), 1.22 (3H, CH$_3$, t, J 7.1) and 1.13 (3H, CH$_3$, t, J 7.1).

3-(2-Azido-2-ethoxy-ethoxy)-benzoic acid

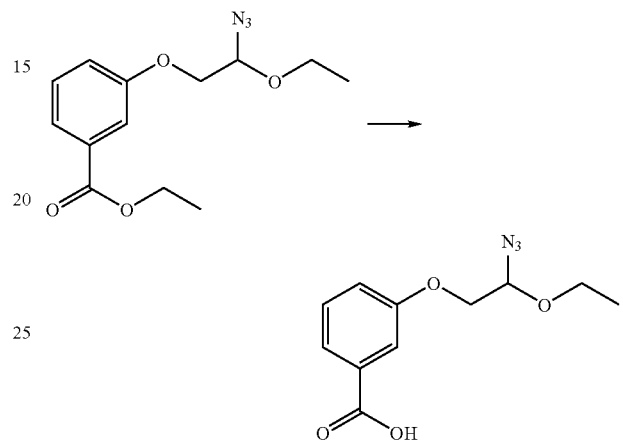

3-(2,2-Diethoxy-ethoxy)-benzoic acid ethyl ester (0.279 g, 1 mmol) was stirred with 4 M aqueous sodium hydroxide (2.5 ml, 10 mmol) and ethanol (2.5 ml) at room temperature. After 4 hrs, all the solvents were removed under reduced pressure and the residue was dissolved in 50 ml water. The solution was acidified with 1 N HCl to pH 2 and then extracted with DCM (3×50 ml). All the DCM extracts were combined, dried over MgSO$_4$ and evaporated under reduced pressure. The title compound was obtained as a colourless solid (0.247 g, 98.4%).

$^1$HNMR [CDCl$_3$]: 7.68 (1H, Ar—H, d J 7.7), 7.58 (1H, Ar—H, dd, J 2.5 and 1.5), 7.34 (1H, Ar—H, t, J 8.0), 7.13 (1H, Ar—H, dd, J 7.4 and 2.7), 4.74 (1H, CHN$_3$, t, J 5.0), 4.20-4.02 (2H, ArOCH$_2$, m), 3.95-3.80 (1H, OCH$_2$, H$_a$, m), 3.70-3.55 (1H, OCH$_2$, H$_b$, m) and 1.24 (3H, CH$_3$, t, J 7.1).

Triethyl ammonium salt of phosphoric acid mono-[5-(5-{3-[3-(2-azido-2-ethoxy-ethoxy)-benzoylamino-prop-1-ynyl}-2,4-dioxo-3,4-dihydro-2H-pyrimidin-1-yl]-3-hydroxy-tetrahydro-furan-2-yl] ester

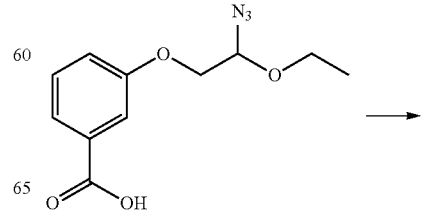

-continued

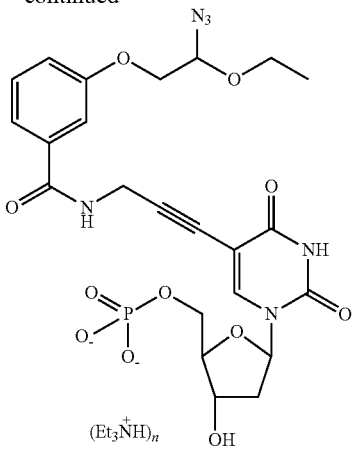

3-(2,2-Diethoxy-ethoxy)-benzoic acid (3.77 mg, 15 µmol) was stirred with N,N'-disuccinimidyl carbonate (3.84 mg, 15 µmol) and 4-dimethylaminopyridine (DMAP) (1.83 mg, 15 µmol) in dry DMF (1 ml) at room temperature. After 15 minutes, all the reaction mixture was added to a solution of the triethyl ammonium salt of phosphoric acid mono-{5-[5-(3-amino-prop-1-ynyl)-2,4-dioxo-3,4-dihydro-2H-pyrimidin-1-yl]-3-hydroxy-tetrahydro-furan-2-yl}ester (5 µmol) in 0.1 M carbonate buffer (0.1 M NaHCO$_3$/0.1 M Na$_2$CO$_3$, v/v, 1:1) (0.5 ml). After 5 hrs at room temperature, the reaction was diluted with 0.05 M triethylammonium bicarbonate (TEAB) buffer (TEAB, pH 7.5) (10 ml). The resulting solution was applied onto a short column of DEAE A-25 (1×5 cm). The column was initially eluted with 0.1 M TEAB buffer (50 ml) and then 0.7 M buffer (50 ml). The 0.7 M TEAB eluents were collected and evaporated under reduced pressure. The residue was co-evaporated with MeOH (2×10 ml) and then purified by preparative HPLC [HPLC gradient: A, 100% 0.1 M TEAB; B 100% MeCN; 0-2 min, 5% B (flow 2-10 ml/min); 2-19 min, 5-40% B (flow 10 ml/min); 19-21 min, 40-95% B (flow 10 ml/min); 21-24 min, 95% B (flow 10 ml/min); 24-26 min, 95-5% B (flow 10 ml/min); 26-30 min, 5% B (flow 10-2 ml/min)]. The product with retention time of 19.6 min was collected and evaporated under reduced pressure and the residue was co-evaporated with methanol (3×5 ml) to give the title compound as triethyl ammonium salt (3.67 mg, yield 80%). $^1$HNMR in D$_2$O indicated approximately 3.2 triethylammonium count ions.

$^1$HNMR [D$_2$O]: 7.89 (1H, H-6, s), 7.44-7.31 (3H, Ar—H, m), 7.28 (1H, Ar—H, m), 7.12 (1H, Ar—H, dt, J 7.1 and 2.3), 6.17 (1H, H-1', t, J 6.9), 4.96 (1H, CHN$_3$, t, J 4.4), 4.43-4.35 (1H, H-3', m), 4.25 (2H, CHN, s), 4.18-4.06 (2H, H-5', m), 4.05-3.90 (1H, H-4', m), 3.89-3.50 (4H, ArOCH$_2$, OCH$_2$, m), 3.03 (19H, CH$_2$N, q, J 7.3), 2.25-2.15 (2H, CH$_2$, m), 1.13 (32H, CH$_3$, t, J 7.3). $^{31}$P [D$_2$O]: 5.17 (s). MS-ES(−), m/z 593 [M−1].

2-(1-Azido-ethoxy)-ethanol

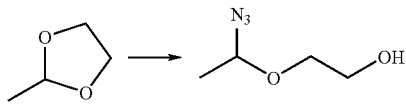

To a mixture of 2-methyl dioxolane (0.897 ml, 10 mmol) and azidotrimethylsilane (1.6 ml, 12 mmol) was added SnCl$_4$ (40 µl) at −78° C. After addition, the cooling bath was removed and the reaction was warmed up to room temperature. After 1 hr, the reaction was worked up by partitioning between DCM (50 ml) and saturated aqueous NaHCO$_3$ (50 ml). The aqueous layer was further extracted with DCM (20 ml). All the DCM extracts were combined, dried over MgSO$_4$ and evaporated under reduced pressure. The residue was dissolved in 10% aqueous methanol. After 2 hr at room temperature, all the solvents were removed under reduced pressure. The title compound was obtained as a colourless oil (224 mg, 17.1%).

$^1$HNMR [CDCl$_3$]: 4.46 (1H, CHN$_3$, q, J 5.7), 3.77-3.68 (1H, OCH$_2$, H$_a$, m), 3.63 (2H, OCH$_2$, t, J 4.3), 3.48-3.40 (1H, OCH$_2$, H$_b$, m) and 1.34 (3H, CH$_3$, d, J 5.7).

[2-(1-Azido-ethoxy)-ethoxy]-acetic acid ethyl ester

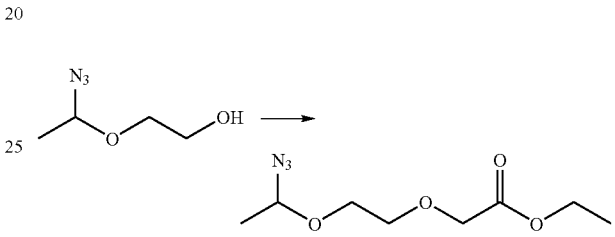

To a solution of 2-(1-azido-ethoxy)-ethanol (0.15 g, 1.14 mmol) in dry tetrahydrofuran (THF) (5 ml) was added NaH (60% dispersion, 0.08 g, 2 mmol) at 0° C. After 15 minutes, ethyl-2-bromoacetate (0.222 ml, 2 mmol) was added. The reaction was maintained at this temperature for 15 minutes and then warmed up to room temperature. The reaction was quenched by addition of saturated aqueous NaHCO$_3$ (5 ml) after 1 hr. After a further period of 5 min, the mixture was partitioned between DCM (50 ml) and saturated aqueous NaHCO$_3$ (50 ml). The aqueous layer was further extracted with DCM (50 ml). All the DCM extracts were combined, dried over MgSO$_4$ and evaporated under reduced pressure. The title compound was obtained as an oil (0.162 g, 65.5%).

$^1$HNMR [CDCl$_3$]: 4.51 (1H, CHN$_3$, q, J 5.6), 4.10 (2H, OCH$_2$, q, J 7.1), 4.03 (2H, OCH$_2$C(O), s), 3.85-3.77 (1H, OCH$_2$, H$_a$, m), 3.67-3.57 (3H, OCH$_2$, H$_b$, OCH$_2$, m), 1.37 (3H, CH$_3$, d, J 5.7) and 1.17 (3H, CH$_3$, t, J 7.1).

[2-(1-Azido-ethoxy)-ethoxy]-acetic acid

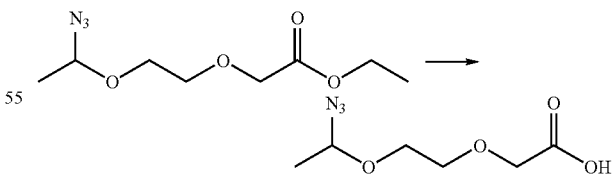

[2-(1-Azido-ethoxy)-ethoxy]-acetic acid ethyl ester (0.10 g, 0.46 mmol) was stirred with 4 M aqueous sodium hydroxide (1.15 ml, 4.6 mmol) and ethanol (1.15 ml) at room temperature. After 4 hrs, all the solvents were removed under reduced pressure and the residue was dissolved in 5 ml water. The solution was adjusted to pH 5 with 1 N KH$_2$PO$_4$ and then extracted with DCM (2×15 ml). The aqueous layer was then acidified with 1 N HCl to pH 2 and then extracted with DCM (3×25 ml). All the DCM extracts were combined, dried over MgSO$_4$ and evaporated under reduced pressure. The title compound was obtained as a colourless solid (42 mg, 48.3%).

$^1$HNMR [CDCl$_3$]: 4.55 (1H, CHN$_3$, q, J 5.7), 4.15 (2H, OCH$_2$C(O), s), 3.92-3.84 (1H, OCH$_2$, H$_a$, m), 3.74-3.70 (2H, OCH$_2$, m), 3.68-3.57 (1H, OCH$_2$, H$_b$, m) and 1.44 (3H, CH$_3$, d, J 5.7).

Triethyl ammonium salt of phosphoric acid mono-{5-[5-(3-{2-[2-(1-azido-ethoxy)-ethoxy]-acetylamino}-prop-1-ynyl)-2,4-dioxo-3,4-dihydro-2H-pyrimidin-1-yl]-3-hydroxy-tetrahydro-furan-2-yl}ester

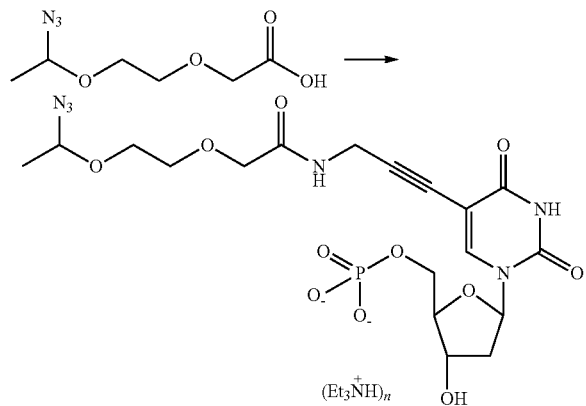

[2-(1-Azido-ethoxy)-ethoxy]-acetic acid (5.7 mg, 30 μmol) was stirred with N,N'-disuccinimidyl carbonate (7.68 mg, 30 μmol) and DMAP (3.7 mg, 30 μmol) in dry DMF (2 ml) at room temperature. After 10 minutes, all the reaction mixture was added to a solution of the triethyl ammonium salt of phosphoric acid mono-{5-[5-(3-amino-prop-1-ynyl)-2,4-dioxo-3,4-dihydro-2H-pyrimidin-1-yl]-3-hydroxy-tetrahydro-furan-2-yl}ester (10 μmol) in 0.1 M TEAB (0.5 ml). After 5 hrs at room temperature, the reaction was diluted with 0.05 M triethylammonium bicarbonate buffer (TEAB, pH 7.5) (10 ml). The resulting solution was applied onto a short column of DEAE A-25 (1×10 cm). The column was initially eluted with 0.1 M TEAB buffer (50 ml) and then 0.5 M buffer (50 ml). The 0.5 M TEAB eluents were collected and evaporated under reduced pressure. The residue was co-evaporated with MeOH (2×10 ml) and then purified by preparative HPLC [HPLC gradient: A, 100% 0.1 M TEAB; B 100% MeCN; 0-2 min, 5% B (flow 2-10 ml/min); 2-15 min, 5-15% B (flow 10 ml/min); 15-28 min, 15-22% B (flow 10 ml/min); 28-30 min, 22-95% B (flow 10 ml/min); 30-34 min, 95% B (flow 10 ml/min); 34-36 min, 95-5% B (flow 10 ml/min); 36-40 min, 5% B (flow 10-2 ml/min)]. The product with retention time of 21.3 min was collected and evaporated under reduced pressure and the residue was co-evaporated with methanol (3×5 ml) to give the title compound as triethyl ammonium salt (9.3 mmol, quantification at λ$_{288}$ in 0.1 M TEAB buffer, 93%). $^1$HNMR in D$_2$O indicated approximately five triethylammonium count ions.

$^1$HNMR [D$_2$O]: 7.85 (1H, H-6, s), 6.15 (1H, H-1', t, J 6.8), 4.75 (1H, CHN$_3$, q, J 5.7), 4.38 (1H, H-3', m), 4.09 (2H, OCH$_2$C(O), s), 3.99 (2H, CHN, s), 3.95 (1H, H-4', m), 3.86-3.60 (6H, OCH$_2$CH$_2$O, H-5', m), 3.03 (30H, CH$_2$N, q, J 7.2), 2.22-2.12 (2H, CH$_2$, m), 1.31 (3H, CH$_3$, d, J 5.7) and 1.11 (45H, CH$_3$, t, J 7.2). $^{31}$P [D$_2$O]: 5.14 (s). MS-ES(−), m/z, 531 [M−1].

3-([1,3]Dioxolan-2-ylmethoxy)-benzoic acid ethyl ester

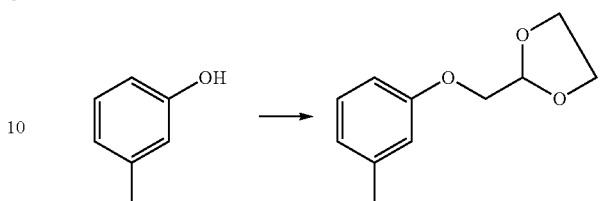

2-Bromomethyl-1,3-dioxolane (8.3 ml, 80 mmol), ethyl-3-hydroxy-benzoate (3.32 g, 20 mmol), potassium carbonate (5.53 g, 40 mmol) and sodium iodide (1.2 g, 8 mmol) were heated at 120° C. in DMF (8 ml) for 17 hrs. The reaction was cooled to room temperature and all the solvents were evaporated under reduced pressure. The residues were partitioned between DCM (250 ml) and water (250 ml). The DCM layer was separated and the aqueous layer was back-extracted with DCM (2×100 ml). All the DCM extracts were combined, dried over MgSO$_4$ and evaporated under reduced pressure. The residue was purified by column chromatography (4×25 cm). The product was eluted with 20% petroleum ether (60-80° C.) in DCM and the title compound was obtained as a slightly brown oil (4.63 g, 91.8%). APCI-MS, m/z 252.95 (M+1).

$^1$HNMR [CDCl$_3$]: 1.39 (3H, CH$_3$, t, J 7.2), 3.96-4.09 (6H, OCH$_2$CH$_2$O, ArOCH$_2$, m), 4.36 (2H, OCH$_2$, q, J 7.2), 5.31 (1H, CH, t, J 4.0), 7.14 (1H, Ar—H, ddd, J 1.6, 2.6 and 8.2), 7.34 (1H, Ar—H, t, J 7.9), 7.59 (1H, Ar—H, dd, J 1.5 and 2.5) and 7.67 (1H, Ar—H, dt, J 1.4 and 7.6).

3-[2-Azido-2-(2-hydroxy-ethoxy)-ethoxy]-benzoic acid ethyl ester

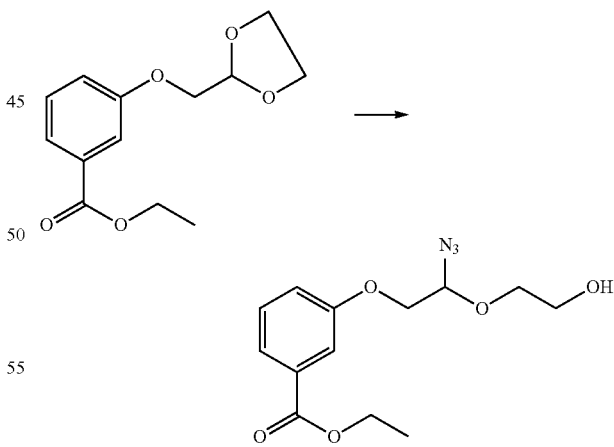

To a mixture of 3-([1,3]-dioxolan-2-ylmethoxy)-benzoic acid ethylester (2.02 g, 8 mmol) and azidotrimethylsilane (1.17 ml, 8.8 mmol) was added SnCl$_4$ (60 μl) at room temperature under nitrogen. After 2 hr, 2% aqueous methanol (10 ml) was added to the reaction mixture and the reaction was stirred at room temperature for 30 minutes. All the solvents were evaporated under reduced pressure. The residue was co-evaporated with ethanol (2×10 ml). The residue was purified by a column chromatography (3×20 cm). The product was eluted with 0 to 1% methanol in DCM. The title compound was obtained as a colourless oil (2.01 g, 85.1%). APCI-MS, m/z 267.90 (M−N₂+1).

¹HNMR [CDCl₃]: 1.38 (3H, CH₃, t, J 7.1), 3.73-3.86 (3H, OCH₂, H$_a$, OCH₂, m), 3.99-4.05 (1H, OCH₂, H$_b$, m), 4.17 (1H, Ar—OCH₂, H$_a$, dd, J 4.9 and 10.1), 4.23 (1H, ArOCH₂, H$_b$, dd, J 5.2 and 10.1), 4.38 (2H, OCH₂, q, 7.1), 4.89 (1H, CH—N₃, t, J 5.1), 7.13 (1H, Ar—H, dd, J 2.1 and 8.4), 7.36 (1H, Ar—H, t, J 7.9), 7.60 (1H, Ar—H, dd, J 1.0 and 2.5) and 7.70 (1H, Ar—H, d, J 7.8).

3-[2-Azido-2-(2-hydroxy-ethoxy)-ethoxy]-benzoic acid

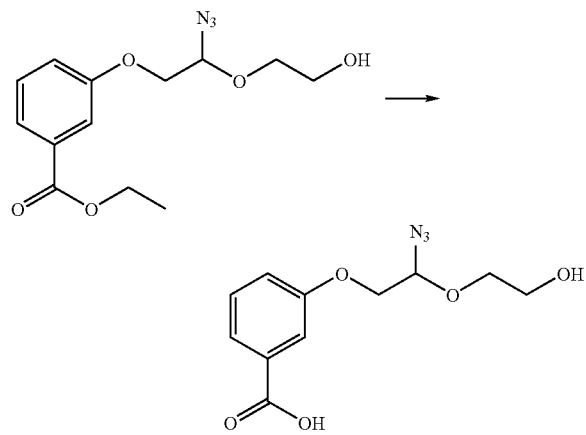

3-[2-Azido-2-(2-hydroxy-ethoxy)-ethoxy]-benzoic acid ethyl ester (1.34 g, 4.55 mmol) was stirred with 4 M aqueous sodium hydroxide (11.4 ml, 45.5 mmol) and ethanol (11.4 ml) at room temperature. After 3 hrs, all the solvents were removed under reduced pressure and the residue was dissolved in 50 ml water. The solution was acidified with 1 N HCl to pH 2 and then extracted with DCM (3×50 ml). All the DCM extracts were combined, dried over MgSO₄ and evaporated under reduced pressure. The title compound was obtained as a colourless solid (1.2 g, 98.7%). ES-MS, m/z 265.85 (M−1).

¹HNMR [CDCl₃]: 3.75-3.90 (3H, OCH₂, H$_a$, OCH₂, m), 4.00-4.08 (1H, OCH₂, H$_b$, m), 4.17 (1H, Ar—OCH₂, H$_a$, dd, J 4.8 and 10.1), 4.24 (1H, ArOCH₂, H$_b$, dd, J 5.1 and 10.1), 4.90 (1H, CH—N₃, t, J 5.1), 7.19 (1H, Ar—H, dd, J 2.5 and 8.2), 7.40 (1H, Ar—H, t, J 8.0), 7.60 (1H, Ar—H, s) and 7.70 (1H, Ar—H, d, J 7.9).

3-[2-Azido-2-(2-ethoxycarbonylmethoxy-ethoxy)-ethoxy]-benzoic acid

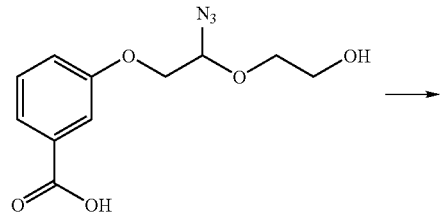

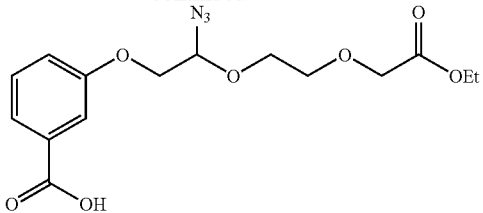

To a solution of 3-[2-azido-2-(2-hydroxy-ethoxy)-ethoxy]-benzoic acid (0.535 g, 2 mmol) in dry THF (6 ml) was added NaH (60% dispersion, 0.246 g, 6 mmol) at 0° C. After 10 minutes, ethyl-2-bromoacetate (0.488 ml, 4.4 mmol) was added. The reaction was then warmed up to room temperature and stirred for 4 hours. The reaction was quenched by pouring it into ice-cold water (50 ml). The mixture was extracted with DCM (2×50 ml) and the DCM extracts were discarded. The aqueous layer was then acidified to pH 2 with 1 N HCl, and extracted with DCM (2×50 ml). These DCM *extracts were combined, dried over MgSO₄ and evaporated under reduced pressure. The residue was purified by column chromatography (1×20 cm). The title compound, eluted with 2% methanol in DCM, was obtained as an oil (0.223 g, 31.6%). ES-MS, m/z 351.95 (M−1).

¹HNMR [CDCl₃]: 1.29 (3H, CH₃, t, J 7.2), 3.81 (2H, OCH₂, t, J 4.4), 3.90 (1H, OCH₂, H$_a$, m), 4.04 (1H, OCH₂, H$_b$, m) 4.13-4.27 (6H, ArOCH₂, OCH₂ and OCH₂C(O)) 4.95 (1H, CH—N₃, m), 7.19 (1H, Ar—H, dd, J 1.7 and 8.3), 7.40 (1H, Ar—H, t, J 7.8), 7.63 (1H, Ar—H, s) and 7.76 (1H, Ar—H, d, J 7.6).

[2-(1-Azido-2-{3-[2-(2,2,2-trifluoroacetylamino)-ethylcarbamoyl]-phenoxy}-ethoxy)-ethoxy]-acetic acid ethyl ester

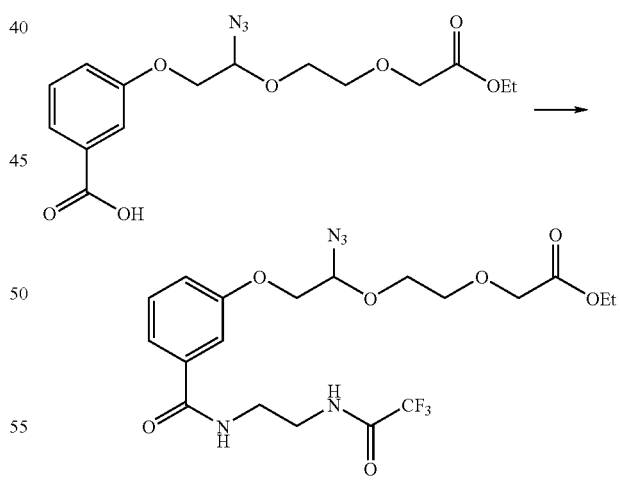

3-[(2-Azido-2-(2-ethoxycarbonylmethoxy-ethoxy)-ethoxy]-benzoic acid (0.212 g, 0.6 mmol) was stirred with N,N'-disuccinimidyl carbonate (0.184 g, 0.72 mmol) and DMAP (0.088 g, 0.72 mmol) in dry DMF (1 ml) at room temperature. After 10 minutes, trifluoroacetic acid salt of N-(2-amino-ethyl)-2,2,2-trifluoro-acetamide (0.194 g, 0.72 mmol) was added followed by diisopropylethylamine (DIPEA) (0.251 ml, 1.44 mmol). The reaction mixture was then stirred at room temperature for 17 hours. All the solvents were evaporated under reduced pressure and the residues were partitioned between DCM (50 ml) and aqueous NaH$_2$PO$_4$ (1 N, 50 ml). The aqueous layer was further extracted with DCM (2×25 ml). All the DCM extracts were combined, dried over MgSO$_4$ and evaporated under reduced pressure. The residue was purified by column chromatography (1×20 cm). The title compound, eluted with 1% methanol in DCM, was obtained as an oil (0.255 g, 86.6%). ES-MS, m/z 490.10 (M−1).

$^1$HNMR [CDCl$_3$]: 1.28 (3H, CH$_3$, t, J 7.1), 3.60 (2H, CH$_2$N, m), 3.69 (2H, CH$_2$N, m), 3.80 (2H, OCH$_2$, t, J 4.3), 3.86 (1H, OCH$_2$, H$_a$, m), 4.04 (1H, OCH$_2$, H$_b$, m), 4.10-4.25 (6H, ArOCH$_2$, OCH$_2$, and OCH$_2$C(O), m), 4.92 (1H, CH—N$_3$, m), 6.85 (1H, NH, br), 7.09 (1H, Ar—H, m), 7.37 (3H, Ar—H, m), and 7.96 (1H, NH, br).

(2-{2-[3-(2-Amino-ethylcarbamoyl)-phenoxy]-1-azido-ethoxy}-ethoxy)-acetic acid

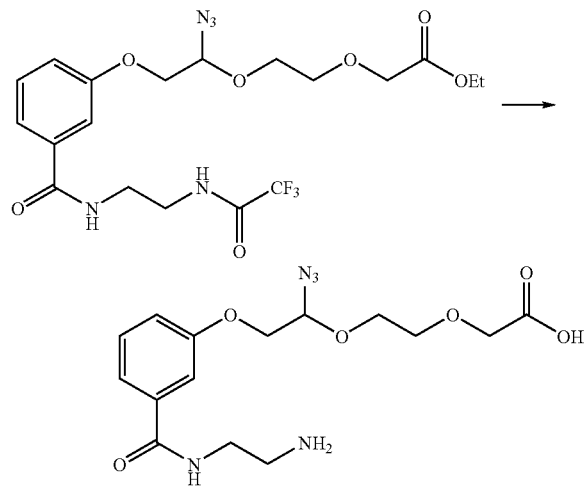

[2-(1-Azido-2-{3-[2-(2,2,2-trifluoroacetylamino)-ethoxycarbamoyl]-phenoxy})ethoxy)-ethoxy]-acetic acid ethyl ester (0.196 g, 0.4 mmol) was stirred with 4 M aqueous sodium hydroxide (1 ml, 4 mmol) and ethanol (1 ml) at room temperature. After 2 hrs, all the solvents were removed under reduced pressure and the residue was dissolved in 15 ml water. The solution was extracted with DCM (2×15 ml). The DCM extracts were discarded and the aqueous layer was acidified with 1 N HCl to pH 2. Then the solution was extracted again with DCM (3×15 ml). The DCM extracts were discarded and the aqueous layer was neutralised with 1 N NaOH to pH 8 and then evaporated under reduced pressure to dryness. The white solids were triturated with DCM/MeOH (v/v; 1:1, 2×25 ml). All the solids were filtered off and the filtrates were combined and evaporated under reduced pressure to give a gum. The gum was added in 10% MeOH in DCM (15 ml) and the insoluble, white solids were filtered off. The filtrates were evaporated under reduced pressure to give the mono-sodium salt of the title compound as a colourless powder (0.135 g, 86.6%). ES-MS, m/z 368.00 (M+1).

$^1$HNMR [D$_2$O]: 3.01 (2H, CH$_2$NH$_2$, t, J 6.0), 3.51 (2H, CH$_2$N, t, J 6.0), 3.62 (2H, OCH$_2$, m), 3.77 (1H, OCH$_2$, H$_a$, m), 3.80 (2H, CH$_2$C(O), s), 3.96 (1H, OCH$_2$, H$_b$, m) 4.19 (2H, ArOCH$_2$, d, J 4.3), 5.01 (1H, CH—N$_3$, t, J 4.5), 7.13 (1H, Ar—H, d, J 7.9) and 7.25-7.39 (3H, Ar—H, m).

[2-(1-Azido-2-{3-[(2-(6-Cy3-hexanoylamino)-ethyl-carbamoyl]-phenoxy}-ethoxy)-ethoxy]-acetic acid

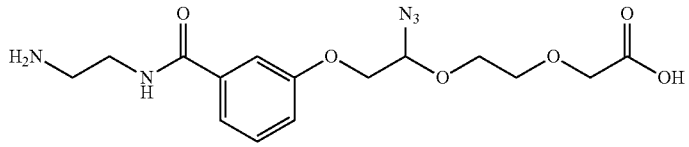

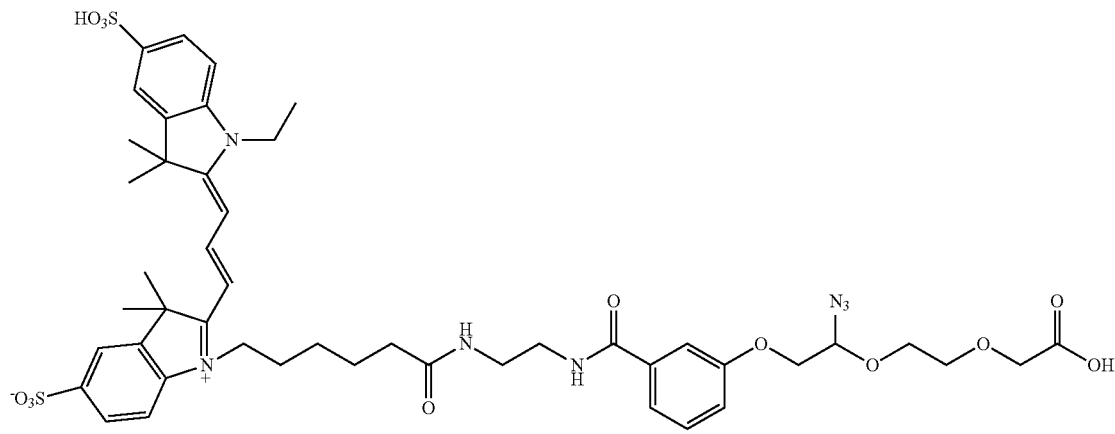

The commercial Cy3 mono N-hydroxysuccinimide ester (5 mg, 6.53 µmol) and (2-{2-[3-(2-amino-ethylcarbamoyl)-phenoxy]-1-azido-ethoxy}-ethoxy)-acetic acid (7.2 mg, 19.6 µmol) were stirred together in dry DMF. DIPEA (6.82 µl, 39.2 µmol) was added. After 2 hr stirring at room temperature, all the solvent was evaporated under reduced pressure. The residue was purified by preparative HPLC [HPLC gradient: A, 100% 0.1 M TEAB; B 100% MeCN; 0-2 min, 5% B (flow 2-10 ml/min); 2-19 min, 5-45% B (flow 10 ml/min); 19-21 min, 45-95% B (flow 10 ml/min); 21-24 min, 95% B (flow 10 ml/min); 24-26 min, 95-5% B (flow 10 ml/min); 26-30 min, 5% B (flow 10-2 ml/min)]. The title compound with retention time of 17.85 min was obtained as a pink solid (4.93 µmol, 75.5%, quantification at 550 nm in water). ES-MS, m/z 488.95 [(M/2)−1]. $^1$HNMR in $D_2O$ indicated approximately 1.8 triethylammonium count ions.

$^1$HNMR [$D_2O$]: 1.15 (16.2H, $CH_3$ ($Et_3N$), t, J 7.2), 1.21 (3H, $CH_3$, t, J 7.1), 1.47 (2H, $CH_2$, m), 1.55 (2H, $CH_2$, m), 1.58 (6H, 2×$CH_3$, s), 1.61 (6H, 2×$CH_3$, s), 2.10 (2H, $CH_2C$(O), t, J 6.5), 3.06 (10.8H, $CH_2$ ($Et_3N$), q, J 7.2), 3.23 (2H, $CH_2N$, t, J 5.5), 3.32 (2H, $CH_2N$, t, J 5.8), 3.56 (2H, $OCH_2$, m), 3.67-3.78 (3H, $OCH_2$, $H_a$ and $CH_2N$, m), 3.79 (2H, $OCH_2C$(O), s), 3.85-3.97 (3H, $OCH_2$, $H_b$ and $CH_2N$, m), 3.98 (2H, Ar$OCH_2$, d, J 4.4), 4.85 (1H, CH—$N_3$, t, J 4.3), 6.14 (1H, =CH, d, J 13.4), 6.19 (1H, =CH, d, J 13.4), 6.90 (1H, Ar—H, m), 7.10-7.19 (5H, Ar—H, m), 7.69 (2H, Ar—H, d, J 8.4), 7.73 (1H, Ar—H, s), 7.77 (1H, Ar—H, s) and 8.36 (1H, =CH, t, J 13.4).

5-[3-(-Cy3-azidolinkeracetylamino)-prop-1-ynyl]-3'-azidomethoxy-dUTP

The reaction mixture was diluted with chilled 0.1 M TEAB (10 ml), the resulting solution was applied onto a short column of DEAE A-25 (1×10 cm). The column was initially eluted with 0.1 M TEAB buffer (50 ml) and then 1.0 M buffer (50 ml). The 1.0 M TEAB eluates were collected and evaporated under reduced pressure. The residue was co-evaporated with MeOH (2×10 ml) and then purified by semi-preparative HPLC [HPLC gradient: A, 100% 0.1 M TEAB; B 100% MeCN; 0-2 min, 5% B (flow 2-5 ml/min); 2-14 min, 5-20% B (flow 5 ml/min); 14-20 min, 20-23% B (flow 5 ml/min); 20-22 min, 23-95% B (flow 5 ml/min); 22-25 min, 95% B (flow 5 ml/min); 25-26 min, 95-5% B (flow 5 ml/min); 26-30 min, 5% B (flow 5-2 ml/min)]. The product with retention time of 19.2 min was collected and evaporated under reduced pressure and the residue was co-evaporated with methanol (3×5 ml) to give the title compound as triethyl ammonium salt (1.22 µmol, quantification at $\lambda_{550}$ in 0.1 M TEAB buffer, 61.1%). $^1$HNMR in $D_2O$ indicated approximately seven triethylammonium count ions.

$^1$HNMR [$D_2O$]: 1.14 (63H, $CH_3$ ($Et_3N$), t, J 7.3), 1.23 (3H, $CH_3$, t, J 7.1), 1.49 (2H, $CH_2$, m), 1.55 (2H, $CH_2$, m), 1.60 (6H, 2×$CH_3$, s), 1.62 (6H, 2×$CH_3$, s), 1.95-2.07 (1H, $H_a$-2', m), 2.13 (2H, $CH_2C$(O), t, J 6.7), 2.17-2.27 (1H, $H_b$-2', m), 3.05 (42H, $CH_2$ ($Et_3N$), q, J 7.3), 3.27 (2H, $CH_2N$, t, J 5.7), 3.37 (2H, $CH_2N$, t, J 5.8), 3.55-3.79 (5H, m), 3.80-4.10 (11H, m), 4.15 (1H, H-4', m), 4.38 (1H, H-3', m), 4.80 (2H, $OCH_2$—$N_3$, s), 4.88 (1H, CH—$N_3$, m), 5.95 (1H, H-1', q, J 7.6), 6.13 (1H, =CH, d, J 13.4), 6.20 (1H, =CH, d, J 13.4), 6.84 (1H, Ar—H, d, J 7.3), 7.05-7.24 (5H, Ar—H, m), 7.60-7.80 (5H, Ar—H and H-6, m) and 8.35 (1H, =CH, t, J 13.4). $^{31}$PNMR [$D_2O$]: −20.82 ($^\beta$P, m), −10.07 ($^\alpha$P, d, J 16.2) and −4.90 ($^\gamma$P, d, J 18.9).

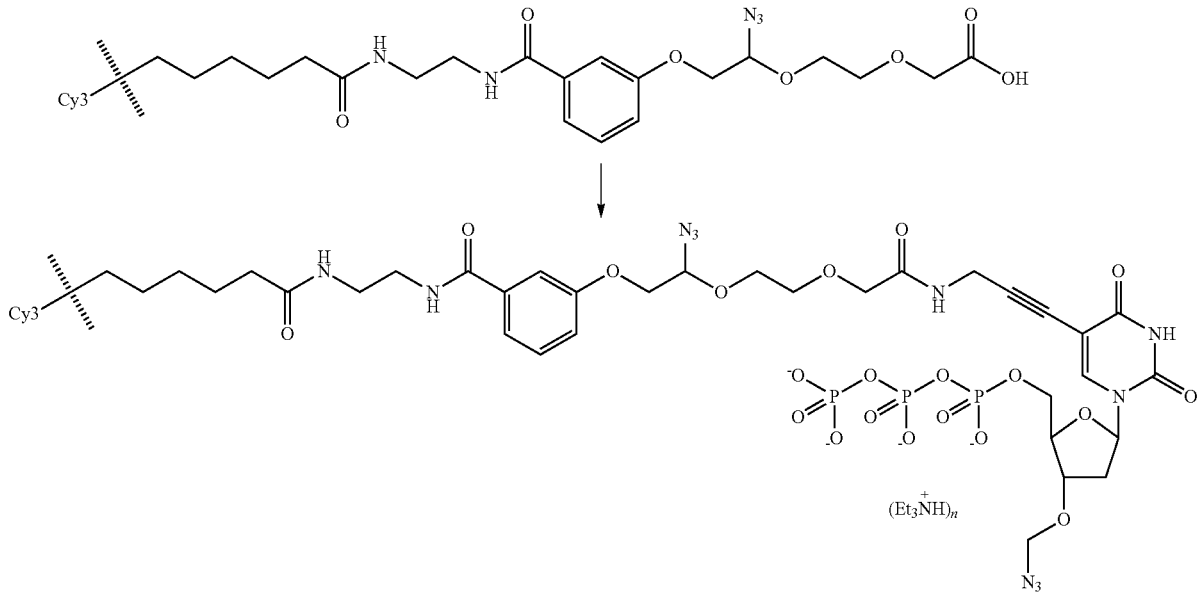

[2-(1-Azido-2-{3-[2-(6-Cy3-hexanoylamino)-ethylcarbamoyl]-phenoxy}-ethoxy)-ethoxy]-acetic acid (2 µmol) was stirred with N,N'-disuccinimidyl carbonate (0.563 mg, 2.2 µmol) and DMAP (0.269 mg, 2.2 µmol) in dry DMF (1 ml) at room temperature. After 10 minutes, all the reaction mixture was added to a solution of the tri-n-butyl ammonium salt of [5-(3-amino-prop-1-ynyl)]-3'-azidomethoxy-dUTP (6 µmol, prepared by evaporating an aqueous solution of [5-(3-amino-prop-1-ynyl)]-3'-azidomethoxy-dUTP with tri-n-butyl amine (72 µl, 300 µmol)). The reaction mixture was sonicated for 5 minutes, then stirred at room temperature for 3 hrs.

2 Cycles of Fully Functional Nucleoside Triphosphate (FFN) Preparation of Beads

Take 15 µL of Dynabeads® M-280 streptavidin coated beads (Dynal Biotech), remove storage buffer and wash 3 times with 150 µL of TE buffer (Tris.HCl pH 8, 10 mM and EDTA, 1 mM). Resuspend in 37.5 µL of B & W buffer (10 mM Tris-HCl pH 7.5, 1 mM EDTA and 2.0 M NaCl), add 10 µL of biotinylated $^{32}$P labelled hairpin DNA and add 27.5 µL of water. Allow to stand at room temperature for 15 minutes. Remove buffer and wash beads 3 times with 100 µL of TE buffer.

Incorporation of the 1st FFN

75 μL reaction, Tris.HCl pH 8.8 50 mM, Tween-20, 0.01%, MgSO$_4$ 4 mM, MnCl$_2$, 0.2 mM, add 2 μM FFN and 100 nM polymerase (*Thermococcus* sp. 9°N exo$^-$ Y409V A485L supplied by New England Biolabs). This solution is then added to the beads and mixed thoroughly and incubated at 65° C. taking 5 μL samples at 3 and 10 minutes and stopping with 5 μL of gel loading buffer (xylene cyanol-bromophenol blue dye solution, Sigma-Aldrich). The reaction mixture is removed from the remaining beads and the beads washed 3 times with 100 μL of TE buffer.

Chase Step

A sample was removed from the incorporation reaction and added to 1 μM of dNTPs (0.25 μM each). This was stopped after 10 minutes by adding 5 μL of gel loading buffer.

Deblocking Step

50 μL of Tris-(2-carboxyethyl)phosphine, trisodium salt (TCEP) 0.1M is added to the beads and mixed thoroughly. The mixture was then incubated at 65° C. for 15 minutes. The deblocking solution is removed and the beads washed 3 times with 100 μL TE buffer. The beads were then resuspended in 50 μL of TE and a 5 μL sample was removed and 5 μL of gel loading buffer)

Incorporation of the 2nd FFN

20 μL reaction, Tris.HCl pH 8.8 50 mM, Tween-20, 0.01%, MgSO$_4$ 4 mM, MnCl$_2$, 0.4 mM, add 2 μM FFN and 100 nM polymerase (*Thermococcus* sp. 9°N exo$^-$ Y409V A485L supplied by New England Biolabs). This solution is then added to the beads and mixed thoroughly and incubated at 65° C. taking 5 μL samples at 3 and 10 minutes and stopping with 5 μL of gel loading buffer.

Chase Step

A sample was removed from the incorporation reaction and added to 1 μM of dNTPs (0.25 μM each). This was stopped after 10 minutes by adding 5 μL of gel loading buffer.

Before loading the samples onto a denaturing 12% acrylamide sequencing gel 0.5 μL of EDTA (0.5 M) was added to each sample and then heated to 95° C. for 10 minutes.

All patents, patent applications, and published references cited herein are hereby incorporated by reference in their entirety. While this invention has been particularly shown and described with references to preferred embodiments, it will be understood by those skilled in the art that various changes in form and details may be made without departing from the scope of the invention encompassed by the claims.

The invention claimed is:

1. A nucleoside or nucleotide comprising a base attached to a detectable label via a cleavable linker, wherein the cleavable linker comprises an azido group.

2. The nucleoside or nucleotide of claim 1, wherein the nucleoside or nucleotide further comprises a dideoxyribose moiety.

3. The nucleoside or nucleotide of claim 1, wherein the nucleoside or nucleotide further comprises a ribose or deoxyribose moiety with a hydroxyl protecting group attached to the 2' or 3' oxygen atom.

4. The nucleoside or nucleotide of claim 3, wherein the linker and protecting group are cleavable under the same conditions.

5. The nucleoside or nucleotide of claim 3, wherein the protecting group is azidomethyl.

6. The nucleoside or nucleotide of claim 1, wherein the base is a purine, pyrimidine or deazapurine.

7. The nucleoside or nucleotide of claim 1, wherein the detectable label is a fluorophore.

8. An oligonucleotide comprising a nucleoside or nucleotide of claim 1.

9. The oligonucleotide of claim 8, wherein the oligonucleotide is attached to a solid support.

10. A solid support comprising the oligonucleotide of claim 8.

11. A composition comprising four nucleosides or nucleotides, wherein each nucleoside or nucleotide comprises a base attached to a detectable label via a cleavable linker, wherein the cleavable linker comprises an azido group and each nucleoside or nucleotide carries a different detectable label.

12. A method for determining the identity of a nucleotide in a target single-stranded polynucleotide, comprising:
    (a) providing one or more of the nucleotides A, G, C and T or U in which each of said nucleotides has a base that is attached to a distinct detectable label via a linker, said linker comprising an azido group; and a polynucleotide complementary to the target polynucleotide, one of said provided nucleotides being suitable for incorporation into said complementary polynucleotide;
    (b) incorporating the nucleotide suitable for incorporation into said complementary polynucleotide; and
    (c) detecting the detectable label, thereby determining the identity of a nucleotide.

13. The method according to claim 12, wherein steps (a) and (b) are repeated one or more times so as to determine the identity of a plurality of bases in the target polynucleotide.

14. The method according to claim 12, wherein step (a) comprises providing four nucleotides and contacting them with the target simultaneously.

15. The method according to claim 12, wherein any unincorporated nucleotides are removed prior to the provision of further nucleotide(s).

16. The method according to claim 12, wherein the linker is cleaved after detecting the label.

17. The method according to claim 16, wherein said cleavage is carried out with a phosphine.

18. The method according to claim 17, wherein said phosphine comprises one or more sulfonate, amine, hydroxyl or carboxylate residues.

19. The method of claim 15, wherein any unincorporated nucleotides are removed prior to detecting step (c).

* * * * *